(12) United States Patent
Robitaille et al.

(10) Patent No.: US 11,291,711 B2
(45) Date of Patent: Apr. 5, 2022

(54) PLASMINOGEN REPLACEMENT THERAPY FOR PLASMINOGEN-DEFICIENCY

(71) Applicant: PROMETIC BIOTHERAPEUTICS, INC., Rockville, MD (US)

(72) Inventors: Martin Robitaille, Saint-Colomban (CA); Karen Thibaudeau, Rosemere (CA); Pierre Laurin, Ville Mont-Royal (CA); Stacy Plum, Arlington, VA (US)

(73) Assignee: PROMETIC BIOTHERAPEUTICS, INC., Rockville, MD (US)

( * ) Notice: Subject to any disclaimer, the term of this patent is extended or adjusted under 35 U.S.C. 154(b) by 371 days.

(21) Appl. No.: 15/771,454

(22) PCT Filed: Nov. 3, 2016

(86) PCT No.: PCT/IB2016/001599
§ 371 (c)(1),
(2) Date: Apr. 27, 2018

(87) PCT Pub. No.: WO2017/077380
PCT Pub. Date: May 11, 2017

(65) Prior Publication Data
US 2019/0231854 A1    Aug. 1, 2019

Related U.S. Application Data

(60) Provisional application No. 62/250,235, filed on Nov. 3, 2015.

(51) Int. Cl.
*A61K 38/48*    (2006.01)
*C12N 9/68*    (2006.01)
(Continued)

(52) U.S. Cl.
CPC .............. *A61K 38/484* (2013.01); *A61P 3/00* (2018.01); *A61P 9/00* (2018.01); *A61P 29/00* (2018.01);
(Continued)

(58) Field of Classification Search
CPC .... A61K 38/482; A61K 38/484; A61K 38/48; C12N 9/6435; C12Y 304/21007
See application file for complete search history.

(56) References Cited

U.S. PATENT DOCUMENTS

| | | | |
|---|---|---|---|
| 4,115,551 A | 9/1978 | Lormeau et al. | |
| 4,996,050 A * | 2/1991 | Tsukada | C07K 16/40 424/94.2 |

(Continued)

FOREIGN PATENT DOCUMENTS

| | | |
|---|---|---|
| WO | 03020297 A2 | 3/2003 |
| WO | 2008027000 A2 | 3/2008 |
| WO | 2016095013 A1 | 6/2016 |

OTHER PUBLICATIONS

Pignataro et al., Pharmacological Research, 2013, 74: 45-48. (Year: 2013).*

(Continued)

*Primary Examiner* — Allison M Fox
*Assistant Examiner* — Qing Xu
(74) *Attorney, Agent, or Firm* — Saliwanchik, Lloyd & Eisenschenk

(57) ABSTRACT

Subjects of the invention are a method of plasminogen supplementation in a plasminogen-deficient subject, and method for the treatment of plasminogen-deficiency in a plasminogen-deficient subject. These methods comprise administering to the plasminogen-deficient subject a dose of plasminogen, and more particularly Glu-plasminogen, for increasing the subject plasminogen activity level by at least
(Continued)

Schema Showing Terminology Used Herein In Relation With Repeated Administration about 1%, and more particularly by at least 10%, of the normal plasminogen activity and for maintaining the plasminogen activity level over a supplementation period or a treatment period. The plasminogen-deficient subject of the present invention may suffer from Type-I, Type-II plasminogen-deficiency or an acquired deficiency.

11 Claims, 16 Drawing Sheets

(51) Int. Cl.
*A61P 3/00* (2006.01)
*A61P 9/00* (2006.01)
*A61P 29/00* (2006.01)

(52) U.S. Cl.
CPC .... *C12N 9/6435* (2013.01); *C12Y 304/21007* (2013.01)

(56) References Cited

U.S. PATENT DOCUMENTS

| | | | |
|---|---|---|---|
| 5,304,383 A | | 4/1994 | Eibl et al. |
| 5,626,841 A | * | 5/1997 | Gurewich ............... A61K 38/49 424/94.63 |
| 5,637,299 A | * | 6/1997 | McDonagh .......... A61K 38/166 424/94.63 |
| 2013/0295012 A1 | * | 11/2013 | Ingber .................. A61K 31/721 424/9.1 |
| 2018/0360930 A1 | * | 12/2018 | Li ........................... A61P 27/02 |

OTHER PUBLICATIONS

Watts et al., American Journal of Ophthalmology, 2002, 133(4):451-455 (Year: 2002).*

Ang, M. J. et al., "Topical Plasminogen as Adjunctive Treatment in Recurrent Ligneous Conjunctivitis" Ophthalmic Plast. Reconstr. Surg., 2017, 33 (2): Abstract.

Heidemann, D. G. et al., "Treatment of ligneous conjunctivitis with topical plasmin and topical plasminogen." Cornea, Nov. 2003, 22 (8): Abstract.

Kraft, J. et al., "Ligneous conjunctivitis in a girl with severe type I plasminogen deficiency." Graefe's Archive for Clinical and Experimental Ophthalmology, Sep. 2000, 238 (9): Abstract.

Schott, D. et al., "Therapy with a Purified Plasminogen Concentrate in an Infant with Ligneous Conjunctivitis and Homozygous Plasminogen Deficiency." The New England Journal of Medicine, Dec. 1998, 339 (23): 1679-1686.

Schuster, V. et al., "Plasminogen Deficiency." Journal of Thrombosis and Haemostasis, Sep. 2007, 5 (12): 2315-2322.

Tefs, K et al., "Molecular and clinical spectrum of type I plasminogen deficiency: a series of 50 patients." Blood, Jul. 2006, 108: 3021-3026.

Watts, P. et al., "Effective treatment of ligneous conjunctivitis with topical plasminogen." American Journal of Ophthalmology, Apr. 2002, 133 (4): Abstract.

* cited by examiner

Example of Generalized Gingival Hyperplasia

With Nodular Enlargement Covered By Pseudomembranes

Schema Showing Terminology Used Herein In Relation With Repeated Administration

Photographs of Subject 2 Right Eyelid Prior (Day 0) and

1 Day After Receiving a Single Dose of 2 mg/kg of Glu-Plasminogen (Day 1)

FIGURE 7A (Day 0)   FIGURE 7B (Day 1)

Plasmatic Plasminogen Activity of Subject 2

After Receiving a Single Dose of 2 mg/kg of Glu-Plasminogen

Chest X-Ray Photograph Showing Total Atelectasis of the Left Lung Due to Airway Obstruction in the Subject of Example 4 Prior to Receiving Glu-Plasminogen Supplementation
FIGURE 12
Bronchoscopy Photographs of the Trachea of the Subject of Example 4 Showing Viscous Secretions (Fig 13 A) and Obstructive Lesions in the Trachea (Fig 13 B)
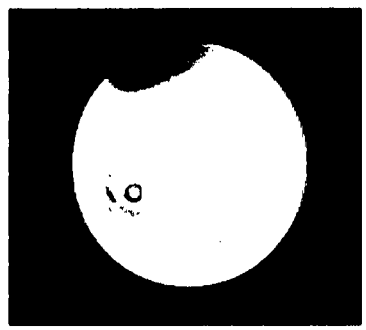 
FIGURE 13A         FIGURE 13B Single Dose of 6 mg/kg of Glu-Plasminogen in Seven Patients Trough Levels in Subject 01-001 (6 mg/kg, q3d)

Clinical Global Impression – Global Improvement (CGI –I) Scale
Rate total improvement whether or not, in your clinical judgment, it is due entirely to drug treatment. Compared to his/her condition at baseline, how much has he/she changed?

☐ 0 = Not assessed
☐ 1 = Very much improved
☐ 2 = Much improved
☐ 3 = Minimally improved
☐ 4 = No change
☐ 5 = Minimally worse
☐ 6 = Much worse
☐ 7 = Very much worse

FIGURE 24

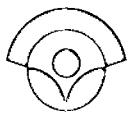

American Chronic Pain Association

Quality Of Life Scale
A Measure Of Function
For People With Pain

| | | |
|---|---|---|
| Non-functioning | 0 | Stay in bed all day<br>Feel hopeless and helpless about life |
| | 1 | Stay in bed at least half the day<br>Have no contact with outside world |
| | 2 | Get out of bed but don't get dressed<br>Stay at home all day |
| | 3 | Get dressed in the morning<br>Minimal activities at home<br>Contact with friends via phone, email |
| | 4 | Struggle but fulfill daily home responsibilities  No outside activity<br>Not able to work/volunteer |
| | 5 | Do simple chores around the house<br>Minimal activities outside of home two days a week |
| | 6 | Work/volunteer limited hours<br>Take part in limited social activities on weekends |
| | 7 | Work/volunteer for a few hours daily. Can be active at least five hours a day. Can make plans to do simple activities on weekends |
| | 8 | Work/volunteer for at least six hours daily<br>Have energy to make plans for one evening social activity during the week<br>Active on weekends |
| | 9 | Work/volunteer/be active eight hours daily<br>Take part in family life<br>Outside social activities limited |
| Normal Quality of Life | 10 | Go to work/volunteer each day<br>Normal daily activities each day<br>Have a social life outside of work<br>Take an active part in family life |

FIGURE 25

PLASMINOGEN REPLACEMENT THERAPY FOR PLASMINOGEN-DEFICIENCY

CROSS REFERENCE TO A RELATED APPLICATION

This application is a National Stage Application of International Application Number PCT/CA2016/001599, filed Nov. 3, 2016; which claims priority to U.S. Provisional Application No. 62/250,235, filed Nov. 3, 2015, both of which are incorporated herein by reference in their entirety.

FIELD OF INVENTION

The present invention relates to the field of medicine. Particular aspects of the invention relates to methods and uses for supplying plasminogen to a plasminogen-deficient subject.

BACKGROUND OF INVENTION

Plasminogen (Pg) is a naturally occurring protein synthesized by the liver and circulates in the blood. Once activated, plasminogen becomes plasmin, an enzymatic component of the fibrinolytic system and the main enzyme involved in the lysis of clots and clearance of extravasated fibrin.

Mechanism of Action of Human Plasminogen:

Physiologically, plasminogen is involved in both intravascular and extravascular fibrinolysis (Castillino and Ploplis, 2005). Two major glycoforms of plasminogen exist in humans plasma: Type 1 plasminogen, which contains two glycosylation moieties (N-linked to N289 and O-linked to T346), and Type 2 plasminogen, which contains only a single 0-linked sugar (O-linked to T346). Type 2 plasminogen is preferentially recruited to the cell surface, whereas Type 1 plasminogen is more readily recruited to blood clots.

Plasminogen is activated to plasmin by cleavage of the Arg561-Val562 peptide bond by either tissue-type plasminogen activator (tPA) or urokinase-type plasminogen activator. This cleavage results in an α-heavy-chain consisting of five kringles with lysine-binding sites and a β light-chain with the catalytic triad His603, Asp646, and Ser741. The active plasmin is involved in the lysis of fibrin clots in the bloodstream. It has been shown that, upon binding to a fibrin clot, the native plasminogen with an N-terminal glutamic acid (Glu-plasminogen) is readily cleaved and converted into a modified Plasminogen (83 kDa) with an N-terminal lysine (Lys-plasminogen) (as shown in FIG. 1). This Lys-plasminogen is a superior substrate for activation by tPA (Fredenburg and Nesheim, 1992).

Need in the Field:

There is no efficient and non-invasive treatment for subjects who suffer from plasminogen-deficiency. There is a need for novel strategies for treating plasminogen-deficiency. Plasminogen supplementation is non-invasive, and unfortunately, there is no plasminogen supplementation therapy that is offered to these plasminogen-deficient subjects. Therefore, there is a need for providing plasminogen supplementation therapy.

Additional features of the invention will be apparent from a review of the discussion, figures and description of the invention herein.

BRIEF SUMMARY OF THE INVENTION

The present invention relates to a method of plasminogen supplementation in a plasminogen-deficient subject, the use of plasminogen for plasminogen supplementation, plasminogen for use in a plasminogen supplementation in a plasminogen-deficient subject, a method for increasing the plasmatic plasminogen activity level of a plasminogen-deficient subject, and the use of plasminogen for the preparation of a medicament for increasing a subject plasminogen activity level.

The present invention relates to the following items:

1. A method for supplementing plasminogen to a plasminogen-deficient subject, wherein the plasminogen-deficient subject has a reduced plasmatic plasminogen activity relative to a normal plasmatic plasminogen activity, the method comprising administering to the plasminogen-deficient subject a repeated effective dose of plasminogen for increasing the subject plasminogen activity level by at least 1% of the normal plasminogen activity and for maintaining said increased subject plasminogen activity level over a supplementation period.
2. The method of item 1, wherein the administered plasminogen is Glu-plasminogen.
3. The method of item 1 or 2, wherein the plasminogen-deficient subject has a Type I plasminogen-deficiency.
4. The method of item 1 or 2, wherein the plasminogen-deficient subject has a Type II plasminogen-deficiency.
5. The method of item 1 or 2, wherein the plasminogen-deficient subject has an acquired plasminogen deficiency.
6. The method of item 5, wherein the acquired plasminogen deficiency is related to Kawasaki disease; thrombolytic event in neonates or children; burns; severe burns; heterotopic ossification; hyaline membrane disease in neonates; neonatal respiratory disease syndrome disseminated intravascular coagulation; sepsis; thrombolytic therapy in adults; stroke; acute lung injury; adult acute respiratory distress syndrome; diabetes; fulminant hepatic failure; Budd-Chiari syndrome; microangiopathic hemolytic anemia; or atypical hemolytic uremic syndrome.
7. The method of item 1 or 2, wherein the reduced plasmatic plasminogen activity is less than or equal to about 70% of the normal plasminogen activity.
8. The method of item 1, wherein the plasminogen-deficient subject suffers from ligneous conjunctivitis.
9. The method of item 2, wherein the Glu-plasminogen is administered daily, every-two-day, every-three-day, every-four-day, every-five-day, twice-a-week or weekly.
10. The method of item 2, wherein the Glu-plasminogen is administered intravenously.
11. The method of item 1 or 2, wherein the subject plasminogen activity level is increased by at least 5% of the normal plasminogen activity and is maintained at said increased subject plasminogen activity level over a supplementation period.
12. The method of item 1 or 2, wherein the subject plasminogen activity level is increased by at least 10% of the normal plasminogen activity and is maintained at said increased subject plasminogen activity level over a supplementation period.
13. The method of item 1 or 2, wherein the subject plasminogen activity level is increased by no more than about 200% of the normal plasminogen activity.
14. The method of item 1 or 2, wherein the subject plasminogen activity level is increased by no more than about 150% of the normal plasminogen activity.

15. The method of item 1 or 2, wherein the subject plasminogen activity level is increased by no more than about 100% of the normal plasminogen activity.
16. The method of item 2, wherein the Glu-plasminogen is administered daily at a dose of at least 0.5 mg/kg of mass of the plasminogen-deficient subject.
17. The method of items 2, wherein the Glu-plasminogen is administered every-two-day at a dose of at least 1.5 mg/kg of mass of the plasminogen-deficient subject.
18. The method of item 2, wherein the Glu-plasminogen is administered twice-a-week at a dose of at least 6 mg/kg of mass of the plasminogen-deficient subject.
19. The method of item 2, wherein the Glu-plasminogen is administered weekly at a dose of at least 45 mg/kg of mass of the plasminogen-deficient subject.
20. The method of item 2, wherein the Glu-plasminogen is administered daily, every-two-day, every-three-day, or every-four-day at a dose of about 2 mg/kg of mass of the plasminogen-deficient subject.
21. The method of item 2, wherein the Glu-plasminogen is administered every-two-day, every-three-day, every-four-day, every-five-day or weekly at a dose of about 6 mg/kg of mass of the plasminogen-deficient subject.
22. The method of any one of items 1 to 21, wherein the administered plasminogen is efficient to i) reduce, treat or prevent a plasminogen-deficiency related lesion, ii) improved an impaired clinical global impression, or iii) improve an impaired quality of life.
23. Use of plasminogen for the preparation of a medicament for supplementing plasminogen to a plasminogen-deficient subject having a reduced plasmatic plasminogen activity relative to a normal plasmatic plasminogen activity, wherein the medicament is for the administration of an effective dose of plasminogen to the plasminogen-deficient subject for increasing the subject plasminogen activity level by at least 1% of the normal plasminogen activity and for maintaining said increased subject plasminogen activity level over a supplementation period.
24. The use of item 23, wherein the administered plasminogen is Glu-plasminogen.
25. The use of item 23 or 24, wherein the plasminogen-deficient subject has a Type I plasminogen-deficiency.
26. The use of item 23 or 24, wherein the plasminogen-deficient subject has a Type II plasminogen-deficiency.
27. The use of item 23 or 24, wherein the plasminogen-deficient subject has an acquired plasminogen deficiency.
28. The use of item 27, wherein the acquired plasminogen deficiency is related to Kawasaki disease; thrombolytic event in neonates or children; burns; severe burns; heterotopic ossification; hyaline membrane disease in neonates; neonatal respiratory disease syndrome disseminated intravascular coagulation; sepsis; thrombolytic therapy in adults; stroke; acute lung injury; adult acute respiratory distress syndrome; diabetes; fulminant hepatic failure; Budd-Chiari syndrome; microangiopathic hemolytic anemia; or atypical hemolytic uremic syndrome.
29. The use of item 23 or 24, wherein the reduced plasmatic plasminogen activity is less than or equal to about 70% of the normal plasminogen activity.
30. The use of item 23 or 24, wherein the plasminogen-deficient subject suffers from ligneous conjunctivitis.
31. The use of item 23 or 24, wherein the medicament is for daily, every-two-day, every-three-day, every-four-day, every-five-day, twice-a-week or weekly administration.
32. The use of item 23 or 24, wherein the medicament is for intravenous administration.
33. The use of item 23 or 24, wherein the medicament is for increasing the subject plasminogen activity level by at least 5% of the normal plasminogen activity and for maintaining said increased subject plasminogen activity level over a supplementation period.
34. The use of item 23 or 24, wherein the medicament is for increasing the subject plasminogen activity level by at least 10% of the normal plasminogen activity and for maintaining said increased subject plasminogen activity level over a supplementation period.
35. The use of item 23 or 24, wherein the subject plasminogen activity level is increased by no more than about 200% of the normal plasminogen activity.
36. The use of item 23 or 24, wherein the subject plasminogen activity level is increased by no more than about 150% of the normal plasminogen activity.
37. The use of item 23 or 24, wherein the subject plasminogen activity level is increased by no more than about 100% of the normal plasminogen activity.
38. The use of item 24, wherein the medicament is for daily administration of a dose of at least 0.5 mg/kg of mass of the plasminogen-deficient subject.
39. The use of items 24, wherein the medicament is for every-two-day administration of a dose of at least 1.5 mg/kg of mass of the plasminogen-deficient subject.
40. The use of item 24, wherein the medicament is for twice-a-week administration of a dose of at least 6 mg/kg of mass of the plasminogen-deficient subject.
41. The use of item 24, wherein the medicament is for weekly administration of a dose of at least 45 mg/kg of mass of the plasminogen-deficient subject.
42. The use of item 24, wherein the medicament is for daily, every-two-day, every-three-day, or every-four-day administration of a dose of about 2 mg/kg of mass of the plasminogen-deficient subject.
43. The use of item 24, wherein the medicament is for every-two-day, every-three-day, every-four-day, every-five-day or weekly administration of a dose of about 6 mg/kg of mass of the plasminogen-deficient subject.
44. The use of any one of items 23 to 43, wherein the administered plasminogen is efficient to i) reduce, treat or prevent a plasminogen-deficiency related lesion, ii) improved an impaired clinical global impression, or iii) improve an impaired quality of life.
45. Use of plasminogen and a measured reduced plasminogen activity, for identifying a plasminogen-deficient subject having a reduced plasminogen activity relative to a normal plasminogen activity, and for supplementing plasminogen to the subject for increasing the subject plasminogen activity level by at least about 1% of the normal plasminogen activity and for maintaining said increased subject plasminogen activity level over a supplementation period.
46. Plasminogen for use in a plasminogen supplementation in a plasminogen-deficient subject having a reduced plasminogen activity relative to a normal plasminogen activity, wherein the plasminogen supplementation is for increasing the subject plasminogen activity level by at least about 1% of the normal plasminogen activity and for maintaining said increased subject plasminogen activity level over a supplementation period.

47. A method for increasing a plasminogen activity level and for maintaining an increased plasminogen activity level over a supplementation period in a plasminogen-deficient subject having a reduced plasminogen activity relative to a normal plasminogen activity, wherein the increase is by at least about 1% of the normal plasminogen activity, said method comprising administering to said plasminogen-deficient subject Glu-plasminogen (i) a dose of about 2.0 mg/kg of mass of the subject daily, every-two-day, every-three-day or every-four-day; (ii) a dose of about 6.0 mg/kg of mass of the subject every-two-day, every-three-day, every-four-day, every-five-day or weekly.

Further aspects of the invention will be apparent to a person skilled in the art from the following description, claims, and generalizations herein.

BRIEF DESCRIPTION OF THE FIGURES

FIG. 7A shows a photograph of right eyelid of Subject 2 at Day 0 (prior to infusion) in the study described in Example 2. FIG. 7B shows a photograph of right eyelid of Subject 2 at Day 1 in the study described in Example 2.

FIG. 12 is a chest X-ray photograph showing total atelectasis of the left lung due to airway obstruction in the subject described in Example 4 before Glu-plasminogen supplementation.

FIGS. 13 A and 13B show bronchoscopy photographs of the trachea of the subject described in Example 4 showing viscous secretions (A) and obstructive lesions in the trachea (B), respectively.

FIG. 24 shows the scale for the global improvement assessment.

FIG. 25 shows the scale for the quality of life assessment.

DETAILED DESCRIPTION OF THE INVENTION

Figure 1:
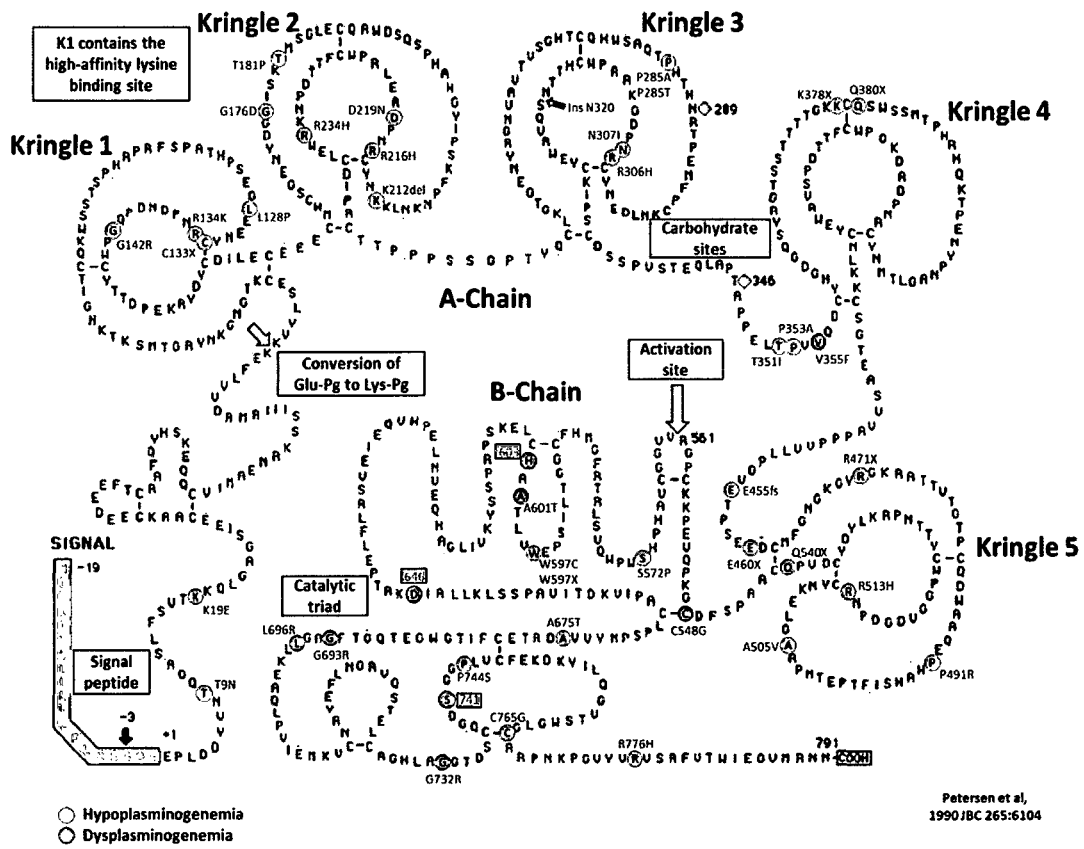
FIG. 1 shows a schematic of the amino acid chain of Glu-plasminogen, its conversion site into Lys-plasminogen, its A- and B-chains, and its Kringle structures.

The present invention concerns a 'plasminogen supplementation', which can be also designated as a 'plasminogen replacement therapy' or a 'plasminogen therapy' or a 'treatment of plasminogen-deficiency'. Plasminogen-deficiency includes congenital plasminogen-deficiency and acquired plasminogen-deficiency.

The present invention concerns a method for i) supplementing plasminogen to a plasminogen-deficient subject or ii) providing said subject with plasminogen, wherein the plasminogen-deficient subject has a reduced plasmatic plasminogen activity relative to a normal plasmatic plasminogen activity, and wherein the method comprises the administration to said subject of an effective dose of plasminogen for increasing the subject plasminogen activity level by at least 1% of the normal plasminogen activity. In a preferred embodiment, the method further comprises a step of determining the plasmatic plasminogen activity of the subject prior to administer plasminogen. In another embodiment, the administration of an effective doses of plasminogen is for increasing the subject plasminogen activity level by at least 1% of the normal plasminogen activity and for maintaining the subject plasminogen activity level superior to said subject plasminogen activity level plus 1% of the normal plasminogen activity over a supplementation period. As such, repeated doses of plasminogen or a continuous administration of plasminogen can be administered in order to maintain said plasminogen activity level above the desired threshold. The related use of plasminogen for the preparation of a medicament for increasing the plasmatic plasminogen activity level of a plasminogen-deficient subject is also an object of the present invention.

In an embodiment, the subject in need of the present invention is a 'plasminogen-deficient subject'. A 'plasminogen-deficient subject' is defined as a subject that has a plasmatic plasminogen activity that is lower than the level of plasmatic plasminogen activity in a non-plasminogen-deficient normal subject (called 'normal plasminogen activity'). Since there is variability in the plasminogen activity of a normal subject, the normal plasminogen activity is preferably calculated in a pool of plasma collected from non-plasminogen-deficient normal subjects or healthy subjects. Said pool of plasma is preferably collected from a sufficiently large amount of subjects so as to normalize the variation found in individuals. Preferably, said pool of plasma is collected from at least 240 non-plasminogen-deficient normal subjects, e.g. 120 healthy male adults and 120 healthy female adults covering ages between 20 and 80 years. In another embodiment, the normal plasminogen activity corresponds to the mean or average plasminogen activity determined in a population of healthy (e.g., not plasminogen-deficient) subjects. Several methods to measure the plasminogen activity are known in the art. For example, plasminogen activity is commonly determined by chromogenic or fluorogenic assays. The pool of subjects for the determination of the normal plasminogen activity as well as the method for measuring the plasminogen activity that are preferably used in accordance with the present invention are described in *Criteria for specific measurement of plasminogen (enzymatic; procedure) in human plasma*, Electronic Journal Of The International Federation Of Clinical Chemistry And Laboratory Medicine, Vol. 12, No. 3, 2000: www.ifcc.org/ifccfiles/docs/plasminogen.pdf.

There are various types of plasminogen-deficient subjects, which include, without limitation, person suffering from i) acute plasminogen deficiency such as new born or premature babies, ii) chronic plasminogen-deficiency patients such as those cause by a mutation, iii) acute neonatal respiratory distress syndrome (NRDS/HMD), iv) acute adults respiratory distress Syndrome (ARDS), v) disseminated intravascular coagulation (DIC), and vi) ligneous conjunctivitis.

According to an aspect of the invention, the subject is human. In embodiments of the invention, the subject is an adult, neonate, infant, children or adolescent.

The term 'reduced plasminogen activity' designates the plasminogen activity measured in a plasminogen-deficient subject. The term 'reduced plasminogen activity' also refer to the plasminogen activity level of a plasminogen-deficient subject prior to the administration of plasminogen in accordance with the present invention. In the case where a subject has Type-I plasminogen-deficiency, its plasmatic plasminogen quantity is lower than the level found in a healthy population and the resulting plasminogen activity is lower than said normal plasminogen activity. In the case where a subject has Type-II plasminogen-deficiency, its plasmatic plasminogen quantity may or may not be lower than the level found in a healthy population; however its plasminogen is mutated such that the resulting plasminogen activity is lower than said normal plasminogen activity. In the case where a subject has a poorly controlled or uncontrolled diabetes mellitus, its plasmatic plasminogen quantity may or may not be lower than the level found in a healthy population; however, its plasminogen is glycosylated such that the resulting plasminogen activity is lower than said normal plasminogen activity. Therefore, in all these cases, the plasminogen activity levels of these subjects are lower than said normal plasminogen activity. In an aspect of the invention, the reduced plasminogen activity is 70% of the normal plasminogen activity or less, 60% of the normal plasminogen activity or less, 50% of the normal plasminogen activity or less, 40% of the normal plasminogen activity or less, 35% of the normal plasminogen activity or less, or 30% of the normal plasminogen activity or less.

It has been determined by the inventors that an effective dose of plasminogen is a dose that increases the plasminogen activity level of a plasminogen-deficient subject by at least about 1% of the normal plasminogen activity. In an embodiment, said effective dose of plasminogen increases the subject plasminogen activity level by at least about 1% of the normal plasminogen activity and maintains said increased subject plasminogen activity level over a supplementation period. In a further embodiment, the effective dose of plasminogen increases the subject plasminogen activity level by at least about 5% of the normal plasminogen activity level. In another embodiment, the effective dose of plasminogen increases the subject plasminogen activity level by at least about 5% of the normal plasminogen activity level and maintains said increased subject plasminogen activity level over a supplementation period. In yet another embodiment, the effective dose of plasminogen increases the subject plasminogen activity level by at least about 10% of the normal plasminogen activity. In another further embodiment, the effective dose of plasminogen increases the subject plasminogen activity level by at least about 10% of the normal plasminogen activity level and maintains said increased subject plasminogen activity level over a supplementation period.

The normal plasminogen activity is arbitrary represented by 100%. Thus, an increase of at least about 10% of the normal plasminogen activity (100%) represents at least about 10%. For example, in the case that a reduced plasminogen activity is determined at 40%, then the increased plasminogen activity after administration of plasminogen is at least about 50%. According to an embodiment of the invention, the reduced plasminogen activity is increased by at least about 10%, about 15%, about 20%, about 25%, about 30%, about 35%, about 40%, about 45%, or about 50% of the normal plasminogen activity.

Figure 4:
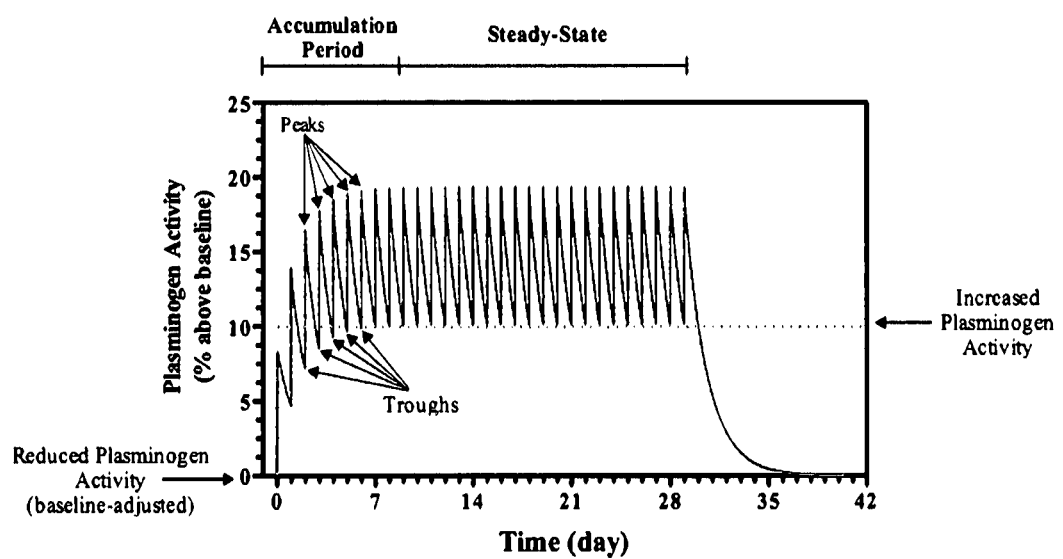
FIG. 4 is a graph showing the terminology used herein in order to describe the phases of a typical repeated administration and 'increased plasminogen activity' in accordance with the present invention.

In an embodiment where the plasminogen activity level is increased to a desired level and is maintained at said desired level over a supplementation period, the dose of plasminogen may be administered in multiple doses so as to build up a plasmatic concentration to the desired level and maintain it. For each dose being administered, there is a peak of plasmatic level that is reached followed by a decrease. Between two administered doses, there is a minimal plasmatic level that is attained, which is called the trough (see FIG. 4). Thus, the peak corresponds to the maximal activity following the administration of one dose; and the trough corresponds to the lowest activity attained between the administrations of two doses (see FIG. 4). Initially, when administering the repeated doses, the plasminogen will accumulate in the plasma to a certain rhythm that depends on its intrinsic half-life of plasminogen in the subject, the amount of plasminogen being administered and the frequency of its administration. The plasmatic level of plasminogen activity will increase during a period called the 'accumulation period' (see FIG. 4), which lasts generally up to 3 to 5 times the half-life of a compound in a subject's plasma. After that accumulation period, the plasminogen elimination and the plasminogen input comes to an equilibrium and the plasmatic level of plasminogen activity stops to increase and reaches a plateau, which is called the 'steady-state' (see FIG. 4). During the steady-state, the trough level remains stable at a particular level. This is the level of the troughs at steady-state that corresponds to the 'increased subject plasminogen activity level' in accordance with the present invention. According to the present invention, the peaks of plasminogen activity at steady-state are higher than the increased plasminogen activity level, and the troughs of plasminogen activity at steady-state define said increased plasminogen activity level. Thus, when the present invention discusses increasing and maintaining the plasmatic plasminogen activity of a subject to a level that is increased by at least about 1% of the normal plasminogen activity, it refers to the level of the troughs obtained by the repeated administration of plasminogen. It should be understood that, according to the present invention, at any time during the steady-state, the plasminogen activity (peaks and troughs) is at least about 1% of the normal plasminogen activity, or at least about 5% of the normal plasminogen activity, at least about 10% of the normal plasminogen activity.

In an embodiment, it is desirable that the peak level of plasminogen activity during the steady-state is not higher than about 8 times the normal plasminogen activity (about 800%), about 5 times the normal plasminogen activity (about 500%), about 3 times the normal plasminogen activity (about 300%), about 2.5 times the normal plasminogen activity (about 250%), about 2 times the normal plasminogen activity (about 200%), about 1.75 times the normal plasminogen activity (about 175%), about 1.5 times the normal plasminogen activity (about 150%), about 1.25 times the normal plasminogen activity (about 125%), or about 1 time the normal plasminogen activity (about 100%). In embodiments, the subject plasminogen activity level is increased by no more than about 200% of the normal plasminogen activity, by no more than about 150% of the normal plasminogen activity, or by no more than about 100% of the normal plasminogen activity. In this case, when the subject plasminogen activity level is increased by no more than about a certain value, it is intended to peak level of the plasminogen activity is not higher than a certain value. In an embodiment, it is desirable that the trough level is higher than a minimal value and the peak level is lower than a maximal value, wherein said minimal value is preferably equal to the subject basal level+1%, 5% or 10% of the normal level; and the maximal value is 100%, 125%, 150%, 175%, 200%, 250%, 300%, 500% or 800% of the normal level.

According to an aspect of the invention, the plasminogen-deficient subject can suffer from a Type I plasminogen-deficiency, a Type II plasminogen-deficiency, or an acquired plasminogen-deficiency. Type I and II plasminogen-deficiencies are designated as congenital plasminogen-deficiencies.

There are Two Types of Congenital Plasminogen-Deficiency:

Type-I plasminogen-deficiency and Type-II plasminogen-deficiency. Hypoplasminogenemia, also known as Type I plasminogen-deficiency, is a rare autosomal recessive disorder characterized by decreased levels of both immunoreactive and functional plasminogen and leading to severe clinical manifestations primarily due to the formation of fibrous depositions on mucous membranes throughout the body (Schott D. et al., 1998 Therapy with a Purified Plasminogen Concentrate in an Infant with Ligneous Conjunctivitis and Homozygous Plasminogen Deficiency. New Engl. J. Med. (339):1679). In Type II plasminogen-deficiency, or dysplasminogenemia, plasminogen antigen levels are normal or slightly reduced, but specific functional plasminogen activity is markedly reduced.

Figure 2:
FIG. 2 shows a photograph of a 4-year old patient suffering from ligneous conjunctivitis in both eyes (Schuster and Seregard, 2003).

The most common and well-defined condition associated with hypoplasminogenemia is ligneous conjunctivitis, which is characterized by thick, woody (ligneous) growths on the conjunctiva of the eye. FIG. 2 shows a photograph of a 4-year old patient suffering from ligneous conjunctivitis at both eyes (Schuster V. and Seregard S. 2003 Ligneous conjunctivitis. Surv. Ophthalmol. 48(4), pp. 369-388).

Left untreated, ligneous conjunctivitis can lead to blindness. Most affected cases of ligneous conjunctivitis are infants and children with plasminogen-deficiency, with the median age of first clinical manifestation at approximately 10 months (Schuster V. et al. 2007 Plasminogen deficiency. J. Thromb. Haemost. 5(12), pp. 2315-2322; Bateman J. B. et al. 1986 Ligneous conjunctivitis: an autosomal recessive disorder. J Pediatr Ophthalmol Strabismus. 23(3), pp. 137-140). Ligneous conjunctivitis is believed to be triggered by local infection or surgical interventions on the eye (Schuster V. and Seregard S. 2003 Ligneous conjunctivitis. Surv. Ophthalmol. 48(4), pp. 369-388).

Figure 3:
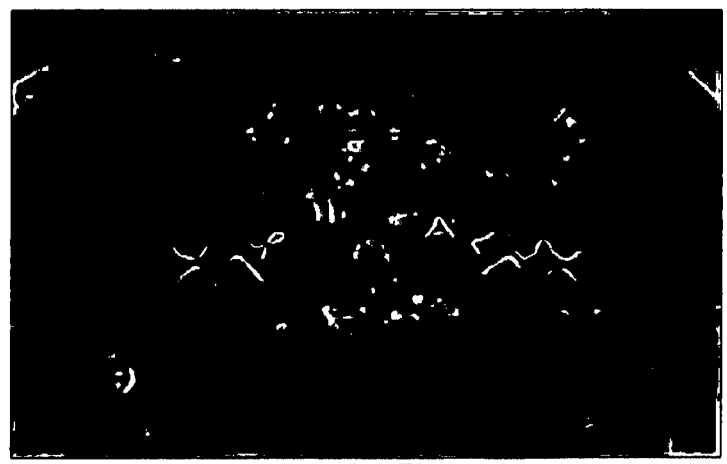
FIG. 3 shows a photograph of a generalized gingival hyperplasia with nodular enlargement covered by yellowish pseudomembranes (Silva, 2006).

In addition to ligneous conjunctivitis, hypoplasminogenemia is a multisystem disease that can also affect the ears, sinuses, tracheobronchial tree, genitourinary tract, and gingiva. FIG. 3 shows a photograph of a generalized gingival hyperplasia with nodular enlargement covered by yellowish pseudomembranes (Silva G. B. et al. Clinical manifestations due to severe plasminogen deficiency: a case report. 2006 J. Dent. Child (Chic). 73(3), pp. 179-82). Tracheobronchial lesions with hyperviscous secretions can result in respiratory failure. In addition, hydrocephalus has been reported in approximately 10% children with severe plasminogen-deficiency, apparently related to the deposition of fibrin in the cerebral ventricular system. Treatment of hydrocephalus may require implantation of a shunt, which may be complicated by repeated occlusions due to the lack of normal clot lysis and result in death. Severely impaired skin wound healing associated with plasminogen-deficiency has also been reported. Although less frequently reported, involvement of gastrointestinal tract, renal system, and a malformation of the cerebellar vermis known as the Dandy-Walker malformation have also been reported (Schott D. et al., 1998 Therapy with a Purified Plasminogen Concentrate in an Infant with Ligneous Conjunctivitis and Homozygous Plasminogen Deficiency. New Engl. J. Med. (339):1679). The prognosis of hypoplasminogenemia varies by the extent, length, and site of lesions and may result in retarded mental growth, loss of organ function, and sometimes death (Mingers A. M. et al. Homozygous type I plasminogen deficiency. 1997 Semin. Thromb. Hemost. 23(3), pp. 259-269; Schuster V. et al. Plasminogen deficiency. 2007 J. Thromb. Haemost. 5(12), pp. 2315-2322; Mehta R. and Shapiro A. D. Plasminogen deficiency. 2008 Haemophilia. 14(6), pp. 1261-1268).

Genetic Basis for Hypoplasminogenemia or Dysplasminogenemia:

Diagnosis of severe hypoplasminogenemia relies on recognition of the clinical manifestations and laboratory test findings of plasminogen activity and antigen levels. Diagnosis can be confirmed by analysis of the plasminogen gene.

The plasminogen gene spans approximately 52.5 kilobases (kb) of DNA and is composed of 19 exons separated by 18 introns. The plasminogen cDNA of 2.7 kb encodes a protein consisting of 791 amino acids. Two exons code for the five kringle domains of plasminogen. Mutations in the plasminogen gene can lead to either Type I plasminogen-deficiency (hypoplasminogenemia), where the circulating plasminogen antigen and activity are reduced, or Type II plasminogen-deficiency (dysplasminogenemia), where the circulating plasminogen activity is reduced but the plasminogen antigen level is normal.

The most common clinical manifestation of Type I plasminogen-deficiency is ligneous conjunctivitis. Mingers, 1997 was the first to demonstrate severely reduced plasminogen antigen and plasminogen activity levels in three unrelated girls with ligneous conjunctivitis. Schuster V. et al. (2007) has identified a homozygous Gly-to-Ala point mutation at exon 7, position 780 in a young female with ligneous conjunctivitis. This mutation leads to an Arg216-to-His exchange. The patient's parents and a sister were all heterozygous for this mutation and demonstrated no signs of clinical manifestations. A second young girl with ligneous conjunctivitis had a homozygous Gly-to-Ala point mutation at exon 15, position 1924, which led to a stop codon (Trp59 to Stop). Again, the patient's parents were both symptom-free and heterozygous for this mutation. The father of this second patient also had a mutation in his second allele in the same codon to yield a Trp597 to Cys (compound heterozygosity). These studies were the first evidence that ligneous conjunctivitis may be caused by mutations in the plasminogen gene. Other mutations that have been identified in ligneous conjunctivitis patients with Type I plasminogen-deficiency include: exon 11, position 1511 (Gly to Thr) in three patients, leading to a stop mutation (Glu460 to Stop); compound-heterozygotes, Lys19 to Glu/Arg513 to His, Lys19 to Glu/Arg216 to His and Lys19 to Glu/Leu128 to Pro; and deletion of a Lys splice site mutation in intron Q in two additional patients. Schuster et al. (2007) found a heterozygous Ala-to-Gly point mutation, leading to a Lys19-to-Glu exchange in two patients and the same homozygous mutation in two other patients.

In a study of 50 plasminogen-deficient patients from 44 families, 40 (80%) had ligneous conjunctivitis, 17 (34%) had ligneous gingivitis and 7 patients had both (Tefs K. et al. Molecular and clinical spectrum of type I plasminogen deficiency: A series of 50 patients. 2006 Blood. 108(9), pp. 3021-3026.). In 15 patients (30%), the disease involved the upper and lower respiratory tract (ears, sinus, larynx, bronchi & and lungs) and in 4 (8%) patients the disease affected the female genital tract. The most common defect of the plasminogen gene in these 50 patients was the Lys19-to-Glu mutation (17 patients [34%]) and the basal plasminogen activity level in these patients varies from 27% to 35% of the normal plasminogen activity level. In patients with other mutations, such as R216H mutation, the plasminogen activity level goes down to 2% of the normal plasminogen activity level. The resulting plasminogen activity level is specific for mutation.

Acquired Plasminogen Deficiency:

Non-genetically related decrease levels of plasminogen referred as acquired plasminogen deficiency, have been shown in several conditions, including but not limited to, disseminated intravascular coagulation (DIC), sepsis, leukemia, hyaline membrane disease, liver disease, Argentine hemorrhagic fever, hyperthyroidism, post L-asparaginase therapy, thrombolytic therapy and surgery. The decrease in plasminogen in some of these conditions may be a negative prognostic sign. There are several mechanisms that may cause an acquired plasminogen deficiency. Increased plasminogen consumption as well as depressed plasminogen synthesis may be the reason for the deficiency observed in severe liver disease. An excessive release of natural plasminogen activators induced by massive stimuli (extensive tissue damage, stress, shock, certain drugs, etc.) could possibly lead to a depleted plasminogen level. For example, degradation of plasminogen into low molecular plasminogen by leukocyte elastase is believed to be the reason for the reduction in functional plasminogen observed in septic subjects and Argentine hemorrhagic fever.

There are various diseases or conditions that represent an acquired plasminogen deficiency, such as:
 a) Kawasaki Disease
 b) Neonates/Children (Thrombolytic Event)
 c) Burns and Severe Burns
 d) Heterotopic Ossification (Myositis Ossificans)
 e) Hyaline Membrane Disease in Neonates/Neonatal Respiratory Disease Syndrome (NRDS)
 f) Disseminated intravascular coagulation (DIC)
 g) Sepsis
 h) Thrombolytic Therapy in Adults
 i) Stroke
 j) Acute Lung Injury (ALI)/Adult(Acute) Respiratory Distress Syndrome (ARDS)
 k) Diabetes (Type: 1, 1.5, 2 and 3)
 l) Liver Disease (Hepatic/Fulminant Hepatic Failure)
 m) Budd-Chiari Syndrome
 n) MicroAngiopathic Hemolytic Anemia (MAHAs)
 o) Atypical Hemolytic Uremic Syndrome<

Kawasaki Disease:

Kawasaki disease is a disease in which blood vessels throughout the body become inflamed. The most common symptoms include a fever that lasts for more than five days and is not controlled by usual medications, large lymph nodes in the neck, a rash in the genital area, and red eyes, lips, palms or bottoms of the feet. In some children, coronary artery aneurysms may form in the heart. If the coronary arteries are involved ongoing treatment or surgery may be required. Without treatment coronary artery problems occur in up to 25% and about 1% die. The heart complications are the most important aspect of Kawasaki disease. It is the main cause of heart disease acquired in childhood in the United States and Japan. Death can occur due either to myocardial infarction secondary to blood clot (thrombosis) formation in a coronary artery aneurysm or to rupture of a large coronary artery aneurysm. Thrombolytic therapy using tissue-type plasminogen activator (t-PA/u-PA) is typically used in thrombolytic events. Plasminogen activator require plasminogen as substrate to produce plasmin that will then initiate the fibrinolytic process on the blood clots causing thrombosis. It has been reported that Kawasaki Disease patients have plasminogen activity levels of only 50% hence limiting the therapeutic benefit of the treatment Kawasaki Disease (Saji B. T. et al., Kawasaki Disease: Current Understanding of the Mechanism and Evidence-Based Treatment. 2017 Ed. Springer ISBN 978-4-431-56039-5). Therefore, Kawasaki patients could benefit from plasminogen supplementation therapy of the present invention to ensure swift resolution of the life/limb threatening thrombolytic event.

Neonates/Children (Thrombolytic Event):

Neonates, infants and sometimes children have 40-50% of plasminogen activity when compared to adults. This low plasminogen level slows the generation of plasmin and reduces the thrombolytic effect of exogenous/endogenous steptokinase, urokinase (u-PA) and tissue plasminogen activator (t-PA) when a thrombolytic event occurs. Venous thrombolytic events (VTE) in neonates/infants/children and occasionally adolescents may benefit from supplementation therapy with plasminogen. Furthermore, there is a recommendation from the American College of Chest Physicians to: "We suggest if thrombolysis is required, tissue plasminogen activator (tPA) is used rather than other lytic agents (Grade 2C), and we suggest plasminogen (fresh frozen plasma) administration prior to commencing therapy (Grade 2C)" (Monagle P. et al. Antithrombotic Therapy and Prevention of Thrombosis, $9^{th}$ ED: ACCP Guidelines Chest 2012; 141(2) (Suppl):e737S-e801S).

Burns and Severe Burns and Heterotopic Ossification (Myositis Ossificans):

Heterotopic ossification (HO) is the presence of bone in soft tissue where bone normally does not exist. The acquired form of HO most frequently is seen with either burn or severe burn, musculoskeletal trauma, spinal cord injury, or central nervous system injury. For example, patients who have recently undergone total hip arthroplasty or have paraplegia after spinal cord injury are at risk for HO.

The term heterotopic ossification (HO) describes bone formation at an abnormal anatomical site, usually in soft tissue. HO can be classified into the following 3 types: Myositis ossificans progressiva (fibrodysplasia ossificans progressiva). This disorder is among the rarest genetic conditions, with an incidence of 1 case per 2 million persons. Transmission is autosomal dominant with variable expression. The condition is characterized by (a) recurrent, painful soft-tissue swelling that leads to HO and (b) congenital malformation of the great toe. Traumatic myositis ossificans. In this condition, a painful area develops in muscle or soft tissue following a single blow to the area, a muscle tear, or repeated minor trauma. Neurogenic heterotopic ossification. This condition is the one that comes to mind when the generic phrase heterotopic ossification is used. Recently, the essential role of plasminogen in preventing HO was discovered during fracture studies in which we also determined that plasminogen is essential for fracture healing. Threshold of plasmin activity required to prevent HO: from these studies we have determined that a circulating level of plasminogen >60% is essential to prevent HO formation following skeletal muscle injury.

Patients possessing burns with a >30% body surface area, experience a 50% decrease in plasminogen levels and an increased incidence in HO formation (Mignemi N et al. Plasminogen is Essential to Prevent Heterotypic Ossification Following Traumatic Muscle Injury. 2016 The FASEB Journal, 30(1) Supplement 83.3). Clearly HO patients and particularly burn patients could benefit from plasminogen supplementation therapy of the present invention to prevent HO formation.

Hyaline Membrane Disease in Neonates/Neonatal Respiratory Disease Syndrome (NRDS):

Hyaline membrane disease (HMD), an older term and the synonym of Infant Respiratory Distress Syndrome (IRDS) or Neonatal Respiratory Distress Syndrome (NRDS), refers to the microscopic appearance of smooth, homogeneous, eosinophilic membranes that line terminal bronchioles and alveolar ducts of neonates. Hyaline membranes are composed of necrotic alveolar cells, plasma transudate, aspirated squamous cells, and significant amount of fibrin. Polymorphonuclear cells may infiltrate the membranes if infection complicates NRDS. Although hyaline membranes may be present as early as 3-4 hours after birth in neonates who later died of NRDS, they are usually well established by 12-24 hours. Hyaline membranes typically organize and separate from the underlying alveolar or bronchial wall at 36-48 hours if high oxygen tension and ventilator pressures are not required, and they are ultimately cleared by alveolar macrophages otherwise this condition may lead to the death of the neonate.

At microscopic examination, the small airways containing the hyaline membranes are surrounded by collapsed acini of the surfactant-deficient lungs. Hence, RDS of the newborn is an acute lung disease that typically affects premature infants and is caused by, primarily, inadequate amounts of surfactant. Decreased surfactant results in insufficient surface tension in the alveolus during expiration, leading to atelectasis, decreased gas exchange, severe hypoxia and acidosis.

The basic defect causing RDS in preterm babies is immaturity of the lungs, particularly of type II pneumocytes. Qualitatively and quantitatively, fetal surfactant is less efficient than adult surfactant in lowering the alveolar surface tension and keeping the alveoli open. Because the lungs are not adequately coated with surfactant it leads to leakage of plasma into the alveolar spaces, with subsequent layering of fibrin and necrotic cells ("hyaline membranes") along the surface of alveolar ducts and respiratory bronchioles. The deposition of hyaline membranes in turn further impedes the passage of oxygen from the alveolar spaces across the respiratory surface into the pulmonary vasculature.

It has been reported that neonates delivered at term have plasminogen activity at around 40% of normal (adults) and premature neonates weighting less than 2000 g have plasminogen activity of only 20% compared to the same control. Hence neonates both pre and full term have naturally low levels of plasminogen but when one combines this fact with the clinical physiopathology of NRDS where the intense deposition of fibrin in the alveoli occurs it leads to the immediate conclusion that these patients could benefit from the plasminogen supplementation therapy of the present invention.

Disseminated Intravascular Coagulation (DIC):

Disseminated intravascular coagulation (DIC) is a clinicopathologic syndrome in which widespread intravascular coagulation occurs as a result of exposure or production of pro-coagulants insufficiently balanced by natural anticoagulant mechanisms and endogenous fibrinolysis. Perturbation of the endothelium in the microcirculation along with stimulated inflammatory cells and release of inflammatory mediators play a key role in this mechanism. DIC may cause tissue ischemia from occlusive microthrombi, and bleeding from the consumption of platelets and coagulation factors and, in some cases, an excessive fibrinolytic response.

There are two phenotypes of disseminated intravascular coagulation (DIC). Although the activation of the tissue factor-dependent pathway as the initial step of the coagulation cascade and the presence of insufficient anticoagulation systems are the same, DIC can be subdivided into the fibrinolytic (hemorrhagic) and antifibrinolytic (thrombotic)

phenotypes. In DIC with the fibrinolytic phenotype, DIC and systemic fibrin(ogen)olysis can coexist.

Treatments of DIC with the fibrinolytic phenotype involve the surgical repair of the trauma, improvement of shock, and the rapid and sufficient replacement of platelet concentrate, fresh frozen plasma, and depleted coagulation factors. Plasma plasminogen activity level is known to decrease as much as 70% (30% residual activity of normal) in disseminated intravascular coagulation (Rutherford E. J. et al. Hematologic principles in surgery. In: Townsend C. M. et al., editors. Sabiston Textbook of Surgery 17$^{th}$ Ed. Philadelphia: Elsevier Saunders; 2004. pp. 113-136; Lackner H. and Javid J. P.

Sepsis:

Sepsis is defined as life-threatening organ dysfunction caused by a dysregulated host response to infection. This definition emphasizes the primacy of the nonhomeostatic host response to infection, the potential lethality that is considerably in excess of a straightforward infection, and the need for urgent recognition. Hence, Sepsis is a potentially life-threatening complication of an infection and occurs when chemicals released into the bloodstream to fight the infection trigger inflammatory responses throughout the body. This inflammation can trigger a cascade of changes that can damage multiple organ systems, causing them to fail. Sepsis is defined as severe when these findings occur in association with signs of organ dysfunctions, such as hypoxemia, oliguria, lactic acidosis, elevated liver enzymes, and altered cerebral function. Nearly all victims of severe sepsis require treatment in an intensive care unit for several days or weeks. If sepsis progresses to septic shock, blood pressure drops dramatically, which may lead to death (Mervyn S. et al. The Third International Consensus Definitions for Sepsis and Septic Shock (Sepsis-3). 2016 JAMA, 315(8), pp. 801-810). Septic and haemorhagic shock carry the risk of high mortality. Failure of microcirculation secondary to alterations of haemostasis and fibrinolysis play a major role in the pathogenesis of shock. In certain cases, the plasminogen was significantly lower in non-survivors by day 1 and plasmin-antiplasmin complex significantly higher by day 4 compared to survivors. It was noted that consecutive increase of endogenous plasminogen over day 4 and 7 was significantly stronger in survivors. Fibrinolysis, as measured by enhanced capacity and responsiveness, is clearly predictive and plays a significant role for survival, possibly due to its clearing function in microcirculation (Helling et al. Clinical Hemorheology and Microcirculation, 2010, 45(2-4), pp. 295-300; Seitz R. et al. Reduced fibrinolytic capacity and its restoration by plasminogen substitution in acute renal failure. 1989 Int. J. Tissue React. 11(1), pp. 39-46). Hence, in sepsis, the level of plasminogen activity is severely decreased and patients could benefit from supplementation therapy with plasminogen to improve their clinical outcome.

Thrombolytic Therapy in Adults:

In adults, before or during thrombolytic therapy with high doses of streptokinase, urokinase or tissue plasminogen activator there is a depletion of plasminogen that may terminate the efficacy of the thrombolytic drugs as plasminogen is the substrate for those activators. Such condition include but limited to stroke. The use of thrombolytic agents should therefore always involve close monitoring of the components of the plasminogen-plasmin system, especially during long-term thrombolytic treatments. In these clinical cases, the patients may benefit from plasminogen supplementation therapy of the present invention where it may lead to a decrease in the clot lysis time and a potential decrease in quantity of plasminogen activator required.

Acute Lung Injury (ALI)/Adult(Acute) Respiratory Distress Syndrome (ARDS):

Acute Lung Disease (ALI) is defined as an acute lung disease with bilateral pulmonary infiltrate in a chest radiograph consistent with the presence of edema and no clinical evidence of left atrial hypertension and a pulmonary wedge pressure of 18 mmHg or less. Additionally, the ratio of arterial oxygen to the fraction of inspired oxygen (PaO2/FiO2) must be 300 mmHg or less, regardless of the level of positive end-expiratory pressure (PEEP). Adult Acute Respiratory Distress Syndrome (ARDS), the most severe form of ALI, and it is defined by a ratio of arterial oxygen to fraction of inspired oxygen of 200 mmHg or less. Although the term ARDS is often used interchangeably with ALI, by strict criteria, ARDS should be reserved for the most severe form of the disease. It is noted that the pathophysiology of NRDS and ARDS are different but presence of fibrin in the alveoli is a common histological finding hence the fibrinolytic system has been impaired in some way and unlike NRDS the pathway in ARDS has not been completely elucidated to this day.

Acute Respiratory Distress Syndrome (ARDS) has a high mortality. From a study conducted to probe the bronchoalveolar lavage fluid (BALF) proteome and identify proteins that differentiate survivors from non-survivors of ARDS. In early-phase ARDS, proteins more abundant in survivors mapped to ontologies indicating a coordinated compensatory response to injury and stress. These included coagulation and fibrinolysis; immune system activation; and cation and iron homeostasis. It was determined that early phase proteins differentiating survivors from non-survivors are candidate biomarkers for predicting survival in ARDS and plasminogen evaluation was reported (Bhargava M. and Becker T.L. Proteomic Profiles in Acute Respiratory Distress Syndrome Differentiates Survivors from Non-Survivors, PLoS ONE 9(10): e109713. In this study, ARDS survivor patients has approximately doubled the plasminogen levels compared to the non-surviving ARDS counterpart. Homeostasis system plays such an important role in ARDS, and plasminogen supplementation therapy of the present invention could be beneficial to ARDS/ALI patients by raising their plasminogen level and increase their likelihood of survival.

Diabetes (Type: 1, 1.5, 2 and 3):

Patients with diabetes have an increased risk of atherothrombotic events with poor short and long-term prognosis following myocardial infarction compared with the nondiabetic population. The formation of an obstructive platelet-rich fibrin clot in a coronary artery represents the final step in the atherothrombotic process, resulting in myocardial infarction. Diabetes is associated with a hypofibrinolytic state, representing one mechanism for increased cardiovascular risk in this population. A number of factors have been implicated in impaired fibrin clot lysis in diabetes, including altered structure of the fibrin network, increased incorporation of antifibrinolytic proteins, and inhibition of the fibrinolytic process. Diabetes is also associated with increased incorporation of plasminogen inhibitor and complement C3 into the clot, with both proteins displaying antifibrinolytic activities. Moreover, plasma concentrations of plasminogen activator inhibitor-1 are elevated in diabetes and insulin-resistant states, which compromises the fibrinolytic process through limiting plasmin generation. All these changes promote inhibition of clot lysis and potentially contribute to the development and severity of ischemic cardiovascular disease in individuals with diabetes.

Peripheral arterial disease (PAD) is a condition characterized by atherosclerotic occlusive disease of the lower extremities. While PAD is a major risk factor for lower-extremity amputation, it is also accompanied by a high likelihood for symptomatic cardiovascular and cerebrovascular disease. Although much is known regarding PAD in the general population, the assessment and management of PAD in those with diabetes is less clear and poses some special issues.

Peripheral artery disease (PAD) is more common in patients with diabetes and around half of patients with a diabetic foot ulcer have co-existing PAD. Atherosclerotic arterial occlusive disease below the level of the inguinal ligament results in a reduction in blood flow to the lower extremity. Peripheral arterial disease in diabetes is a condition predominantly of the infra-inguinal vasculature and is distinct from that in patients without diabetes in its characteristics, treatment and outcomes. Identifying PAD among patients with foot ulceration is important because its presence is associated with worse outcomes, such as a slower (or lack of) healing of foot ulcers, lower extremity amputations, subsequent cardiovascular events and premature mortality. Diagnosing PAD is challenging in patients with diabetes, as they frequently lack typical symptoms, such as claudication or rest pain, even in the presence of severe tissue loss. Arterial calcification, foot infection, oedema and peripheral neuropathy, each of which is often present with diabetic foot ulceration, and may adversely affect the performance of diagnostic tests for PAD.

Plasminogen activity in diabetic patients has been investigated and it was found that diabetes was associated with an impaired plasma fibrin network lysis, which has been partly normalized upon improving glycaemia. It was concluded that glycation of plasminogen in diabetes directly affects fibrinolysis by decreasing plasmin generation and reducing protein-specific activity (Ramzi A. and Gamlen T. Diabetes is associated with posttranslational modifications in plasminogen resulting in reduced plasmin generation and enzyme-specific activity. 2013 Blood (122) pp. 134-142). Supplementation plasminogen therapy of the present invention could be used to resorb the hypofibrinolytic state of those diabetic patients and lead to improvements in their overall clinical prognosis.

Liver Disease (Hepatic/Fulminant Hepatic Failure) and Budd-Chiari Syndrome:

Abnormalities of blood coagulation and fibrinolysis are a major part of fulminant liver failure. In a reported study, the fibrinolytic system was determined in 42 patients with this condition (Pernambuco J. R. et al. Activation of the fibrinolytic system in patients with fulminant liver failure. 1993 Hepatology 18(6), pp. 1350-1356). Admission levels of plasma plasminogen activity were low (9.1% of normal). Tissue plasminogen activator activity was found at normal levels, whereas the level of its fast inhibitor, plasminogen activator inhibitor-1, was greatly increased compared with that of controls indicating a shift toward inhibition of fibrinolysis in these patients. High plasma levels of D-dimer, a fragment of cross-linked fibrin, were also found correlating with the increased level of thrombin-antithrombin complex. It was concluded that there are gross abnormalities of the fibrinolytic system in fulminant liver failure, but because inhibitory activity appears to be present in adequate quantities, this limits the incidence of bleeding due to fibrinolysis.

Budd-Chiari syndrome is a liver disease condition caused by occlusion of the hepatic veins that drain the liver. It presents with the classical triad of abdominal pain, ascites, and liver enlargement. The formation of a blood clot within the hepatic veins can lead to Budd-Chiari syndrome. The syndrome can be fulminant, acute, chronic, or asymptomatic Thrombosis is the major risk factor for death in patients with paroxysmal nocturnal hemoglobinuria and previous case reports indicate that venous thrombosis (e.g.: liver) in patients with paroxysmal nocturnal hemoglobinuria is amenable to thrombolysis.

In patients selected for treatment of a Budd-Chiari Syndrome, tPA was administered as an intravenous infusion and fresh-frozen plasma (FFP) when a low plasminogen level was thought to be limiting for tPA-stimulated fibrinolytic activity (Araten D. J. et al. 2012 Thrombolytic therapy is effective in paroxysmal nocturnal hemoglobinuria. Haematologica 97(3), pp. 344-352). It is recommended to closely monitor the plasminogen activity level. FFP has certain limitations, one of which the limited amount of plasminogen/ml of FFP and the introduction of several other proteins that may be non-necessary and even detrimental to the treatment. Hence Budd-Chiari and liver disease patients could benefit from plasminogen supplementation therapy of the present invention.

MicroAngiopathic Hemolytic Anemia (MAHAs): Atypical Hemolytic Uremic Syndrome (aHUS):

Atypical Hemolytic Uremic Syndrome (aHUS) is a thrombotic microangiopathy caused by uncontrolled activation of the alternative pathway of complement at the cell surface level that leads to microangiopathic hemolytic anemia, thrombocytopenia, and acute kidney failure. In approximately one half of affected patients, pathogenic loss-of-function variants in regulators of complement or gain-of-function variants in effectors of complement are identified, clearly implicating complement in aHUS. However, there are strong lines of evidence supporting the presence of additional genetic contributions to this disease. Novel aHUS-associated genes are attempted to be identified, by completing a comprehensive screen of the complement and coagulation pathways in 36 patients with sporadic aHUS using targeted genomic enrichment and massively parallel sequencing. Several genes in the coagulation pathway were also identified as important in the pathogenesis of aHUS. Plasminogen in particular, carried more pathogenic variants than any other coagulation gene, including three known plasminogen deficiency type 1 mutations and a predicted pathogenic variant. Bu F. et al. (Bu et al. Comprehensive genetic analysis of complement and coagulation genes in atypical hemolytic uremic syndrome. 2014 J. Am. Soc. Nephrol.; 25(1), pp. 55-64) have postulated that, amongst pharmacological possibilities, the stage 1 or the initiator by trigger of the onset of aHUS may be low levels of plasminogen due to the various variants identified in their study. Therefore, plasminogen supplementation therapy of the present invention could benefit in this patient population.

Plasminogen Supplementation Therapy:

Subjects suffering from plasminogen-deficiency including any one of Type I plasminogen-deficiency, Type II plasminogen-deficiency, and acquired plasminogen-deficiency, can take advantage of the supplementation regimen of the present invention. According to an embodiment of the invention where the subject has Type I plasminogen-deficiency, the reduced plasminogen activity of a plasminogen-deficient subject may be about 70% or less, about 60% or less, about 50% or less, about 40% or less, about 35% or less, or about 30% of the normal plasminogen activity or less. Some subjects have a very low level of plasmatic plasminogen activity level, which can be below 5% of the normal plasminogen activity. In these cases, the situation can become life-threatening and the need for plasminogen supplementation can be urgent. In these cases, a high level of peaks can be tolerated and/or a supplementation with a high frequency of administration can be designed so as to accumulate plasminogen in plasma to the desired level as quickly as possible. According to another embodiment of the invention where the subject has Type II plasminogen-deficiency, the reduced plasminogen activity of a plasminogen-deficient subject could be about 70% or less, about 60% or less, about 50% or less, about 40% or less, about 35% or less, or about 30% or less of the normal plasminogen activity.

According to an embodiment of the invention, the plasminogen-deficient subject suffers from ligneous conjunctivitis. Ligneous conjunctivitis is characterized by markedly impaired extracellular fibrinolysis leading to the formation of ligneous (woody) pseudomembranes on mucosal surfaces, including the eye, mouth, sinuses, skin, tracheobronchial tree, gastrointestinal tract, bronchopulmonary tree, and genitourinary tract. Plasminogen-deficiency can also affect the oropharynx, respiratory organs, genitourinary organs, and the skin (juvenile colloid milium). The ligneous (woody) pseudomembranes on mucosal surfaces is also called herein a lesion or a 'plasminogen-deficiency related lesion'. Plasminogen-deficiency is also associated with congenital occlusive hydrocephalus.

In an aspect of the present invention, the increased plasminogen activity is maintained by the administration of repeated effective doses of plasminogen, and more particularly, Glu-plasminogen. Said repeated doses are administered more than once a day, daily, every-two-day, every-three-day, twice-a-week, every-four-day, every-five-day or weekly. It may be desirable to opt for a high frequency of administration during the accumulation period so as to reach the desired level quickly and then reduce the frequency of administration to a desired rate. In another embodiment, the frequency of administration may be decreased after a certain period if the some clinical benefits are achieved. Alternatively, in another embodiment, the frequency of administration may be increased after a certain period if the some clinical benefits are not achieved. In another embodiment, the frequency of administration may remain the same during the whole supplementation period i.e. the accumulation period and the steady-state.

In an embodiment of the invention, plasminogen is administered by one of the following routes of administration: intravenous, intraperitoneal, subcutaneous, nasal, pulmonary, or rectal, wherein the subcutaneous administration is adapted for slow release delivery, continuous delivery or multiple delivery. In an embodiment, plasminogen is administered intravenously. In another embodiment, the subcutaneous administration is performed with an implant containing a slow release formulation or a pump for continuous injection or multiple injections. In a further embodiment, plasminogen is administered subcutaneously and in a continuous manner so that the desired increase in plasminogen activity level is reached and maintained. For instance, a continuous subcutaneous infusion can be used so as to increase and maintain the desired plasminogen activity level in accordance with the present invention.

According to an embodiment, plasminogen is preferably administered daily at a dose of at least about 0.5 mg/kg, at least about 1 mg/kg, at least about 1.5 mg/kg, or at least about 2 mg/kg of the plasminogen-deficient subject mass. According to another embodiment, plasminogen is preferably administered every-other-day at a dose of at least about 1.5 mg/kg, at least about 2 mg/kg, at least about 2.5 mg/kg, at least about 3 mg/kg, at least about 4 mg/kg, at least about 5 mg/kg or at least about 6 mg/kg of the plasminogen-deficient subject mass. According to a further embodiment, plasminogen is preferably administered twice-a-week, every-two-day, every-three-day, every-four-day, every-five-day or weekly at a dose of at least about 2 mg/kg, 3 mg/kg, 4 mg/kg, 5 mg/kg, 6 mg/kg, 7 mg/kg, 8 mg/kg, 9 mg/kg, or 10 mg/kg of the plasminogen-deficient subject mass. According to yet another embodiment, plasminogen is preferably administered weekly at a dose of at least about 45 mg/kg of the plasminogen-deficient subject mass. According to another further embodiment, plasminogen is administered at a dose from about 1.5 mg/kg to about 12 mg/kg and at a frequency from once-a-day to once-a-week.

The present invention concerns the use plasminogen and more particularly human Glu-plasminogen, which is known to have a half-life of about 2.2 days in normal non plasminogen-deficient subjects. The Glu-plasminogen composition comprises preferably a highly purified Glu-plasminogen that is more than about 70%, more than about 80%, more than about 90% or more than about 95% pure. Plasminogen can be produced recombinantly or prepared by purification from plasma. Plasminogen used in the studies described herein was prepared by the method described in PCT publication WO 2006/120423.

In an embodiment of the present invention, plasminogen is not radiolabelled. In an embodiment of the present invention, plasminogen is comprised in a pharmaceutical composition which is free or substantially free of an additional protein. In an embodiment of the present invention, plasminogen is comprised in a pharmaceutical composition which is free or substantially free of albumin. In an embodiment of the present invention, plasminogen is comprised in a pharmaceutical composition which is free or substantially free of aprotinin. In an embodiment of the present invention, plasminogen is comprised in a pharmaceutical composition which is substantially free of a trypsin inhibitor. In an embodiment of the present invention, plasminogen is comprised in a pharmaceutical composition which is free or substantially free of a serine protease inhibitor. In an embodiment of the present invention, plasminogen is comprised in a pharmaceutical composition which is free or substantially free of plasmin. In an embodiment of the present invention, plasminogen is comprised in a pharmaceutical composition which is free or substantially free of a surfactant, for instance, a concentration of surfactant that is less than 0.01 mM.

In an embodiment of the present invention, plasminogen is comprised in a pharmaceutical composition having a purity of about 70% or more, of about 80% or more, of about 85% or more, of about 90% or more, of about 95% or more, and of about 98% or more. In another embodiment of the present invention, plasminogen is comprised in a pharmaceutical composition where the total amount of protein other than plasminogen is less than about 30%, less than about 20%, less than about 15%, less than about 10%, less than about 5%, or less than about 2%.

According to the present invention, the 'supplementation period' may vary. In an embodiment, the supplementation period is at least 48, 72, 96, 120 or 144 hours. In another embodiment, the supplementation period is a life-time. In a further embodiment, the supplementation period stops when the desired clinical benefits are obtained. Optionally, another supplementation period may start upon further clinical benefits are needed. According to the present invention, the 'supplementation period' may vary and be established by a practitioner.

In the present disclosure, the plasminogen activity is either reported as measured or in a baseline-adjusted manner. The baseline-adjusted plasminogen activity is the value of the measured plasminogen activity minus the value of the plasminogen activity before the plasminogen supplementation has started. The plasminogen activity before the plasminogen supplementation has started, can be designated as the basal plasminogen activity, the plasminogen activity at Day 0, or prior the administration of a first plasminogen dose. Thus, baseline-adjusted plasminogen activity shows only the increase of plasminogen activity resulting from the Glu-plasminogen administration.

In some embodiments, the plasminogen quantity is calculated by measuring the plasminogen antigen by ELISA, nephelometry, or radial immunodiffusion.

The efficacy of the plasminogen activity generated by the plasminogen supplementation of the present invention can be demonstrated by clinical observations, as mentioned above, and also by the level of D-dimers. The D-dimers are fibrin degradation fragments resulting from the activity of the plasminogen that degrades fibrin. An increased D-dimer level is representative of i) the presence of lesions and ii) the fibrinolytic efficacy of the administered plasminogen.

In an embodiment, the above-mentioned method comprises measuring the plasminogen activity in a sample from a subject to determine whether said subject is plasminogen-deficient, and if the subject is plasminogen-deficient, performing the method of plasminogen supplementation or treating plasminogen-deficiency described herein in said subject.

EXAMPLES

The following examples further illustrate the practice of this invention but are not intended to be limiting thereof.

Example 1: Glu-Plasminogen Formulation

Glu-Plasminogen is highly purified (>95% purity) from pooled human plasma that is sourced from FDA/EMA-licensed US plasma collection centers. The plasminogen monomer is present as greater than 95%. The Glu-plasminogen was prepared as described previously in PCT publication WO 2006/120423.

Human plasminogen is comprised of approximately 75 milligrams per vial of lyophilized plasminogen. Prior to infusion, the lyophilized powder in a vial is reconstituted with 12.5 mL of water for intravenous injection. The final composition contains sodium citrate, sodium chloride, glycine and sucrose for providing an acceptable protein stability, ionic strength and pH.

Example 2a: Single Dose (2 mg/kg) of Glu-Plasminogen in Pg-Deficient Human Subjects & PK The study described herein is the first study of human Glu-plasminogen in Type-I plasminogen-deficient human patients. The study is a phase 1, non-randomized, open-label, single-dose study in patients diagnosed with hypo-plasminogenemia. Three human adults and two adolescents have received a single dose of 2 mg/kg of Glu-Plasminogen by intravenous (IV) infusion. The infusion time was 10 minutes.

Plasminogen activity and antigen levels were measured so as to draw the plasminogen PK profile. These blood samples were tested at the following time points: Screening (Visit 1, Day −19); Baseline immediately before dosing (Visit 2, Day 0); at 5-15 minutes, 1 hour, 6 hours (Day 1), 24 hours (Visit 3, Day 2), 48 hours (Visit 4, Day 3), 72 hours (Visit 5, Day 4), 96 hours (Visit 6, Day 5), 120 hours (Visit 7, Day 6), 168 hours (Visit 8, Day 8), and 216 hours (Visit 9, Day 10) after the end of infusion. Subjects have returned 30 days after dosing at Visit 11 (Day 31, Follow-up-Safety Visit) for collection of adverse events, immunogenicity testing, routine safety tests and procedures, and final viral safety testing. No adverse event has been reported.

The plasminogen antigen levels and the plasminogen activity levels for all subjects, measured at the screening (Day −19) and prior to the infusion (Day 0) and reported in Table 1. The plasminogen activity level measured prior to the infusion is used to determine the baseline of the pharmacokinetic profile. The plasminogen activity was calculated as the percentage of activity relative to the plasminogen activity level from pooled plasma of healthy subjects. The plasminogen antigen was measured by ELISA assay using the Human Plasminogen Total Antigen Assay ELISA Kit of Cell Sciences®. It can be noted that there may be a variability of the endogenous plasminogen activity level within a subject which some subjects remain relatively stable, as evidenced by the variations of plasminogen activity observed at Day −19 and Day 0 in the same subject (Table 1).

TABLE 1

| | Plasminogen antigen levels (mg/dL) | | Plasminogen activity levels (%) | |
|---|---|---|---|---|
| | Screening | Baseline | Screening | Baseline |
| Subject 1 | 2 | 3 | 35 | 31 |
| Subject 2 | 3 | 5 | 37 | 36 |
| Subject 3 | 4 | 5 | 33 | 36 |
| Subject 4 | 4 | 8 | 39 | 38 |
| Subject 5 | 9 | 15 | 29 | 32 |

Figure 5:
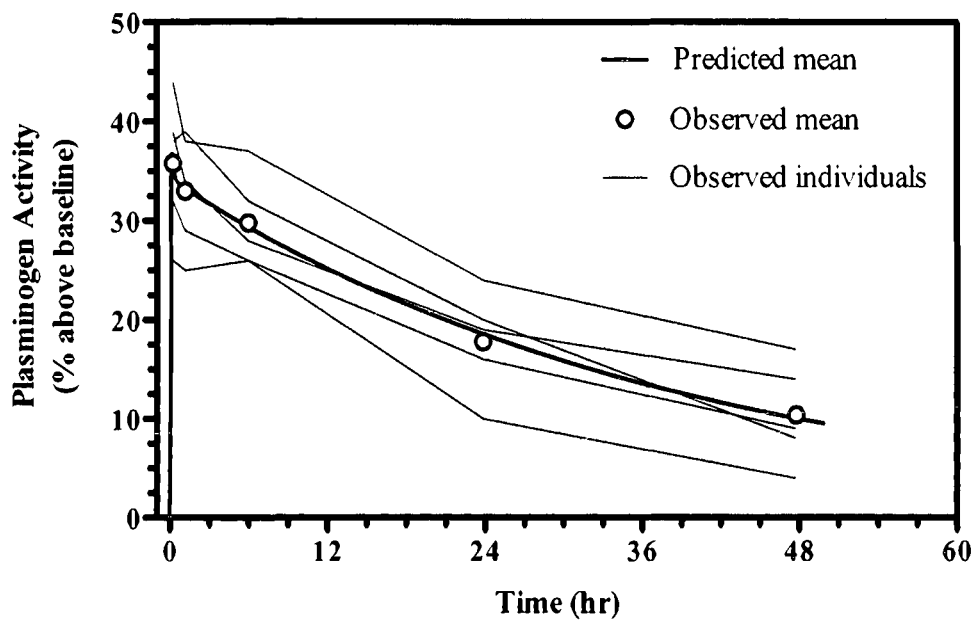
FIG. 5 is a graph showing the pharmacokinetic profile (PK) of the plasmatic plasminogen activity in five plasminogen-deficient subjects that have received a single dose of 2 mg/kg of Glu-plasminogen, the mean value thereof and a predicted PK established from an equation determined by Phoenix® WinNonlin application based on said mean value.

After the plasminogen infusion, the plasminogen activity levels of each subject were adjusted with their own baseline value (Day 0) by subtracting the baseline value so as to obtain the baseline-adjusted plasminogen activity level. Said baseline-adjusted plasminogen activity levels for each subject (thin line) during 48 hours are shown in FIG. 5 together with the mean value (opened circle) for each time point and the predicted pharmacokinetic curve calculated with the application Phoenix® WinNonlin (version 6.4) of Pharsight Corporation. The application Phoenix® WinNonlin uses the mean values of the tested subjects and the study parameters and generates one or more equations and the related curves for predicting a compound's PK. The PK model that corresponds perfectly with the mean values was selected and shown in FIG. 5 (thick line). The observed mean values confirm that the administration of 2 mg/kg of Glu-plasminogen has resulted in a mean plasminogen activity level that is increased (relative to the baseline) by at least 10% of the normal plasminogen activity for a duration of 48 hours.

Example 2b: Single Dose (2 mg/kg) of Glu-Plasminogen in Pg-Deficient Human Subjects & Efficacy Among the Phase 1 study described in Example 2a, Subject 2 had a ligneous conjunctivitis in the eyelid of the right eye. Photographs of the lesion at Day 0 (prior to infusion) and at Day 1 are shown at FIGS. 7A and 7B, respectively. It was noted that the hump caused by the ligneous conjunctivitis has resorbed 24 hours after the plasminogen infusion. Although one case of ligneous conjunctivitis regression is not statistically significant, this observation is nevertheless encouraging and provides evidence of the clinical effect of the present Glu-plasminogen replacement therapy.

Figure 7C:
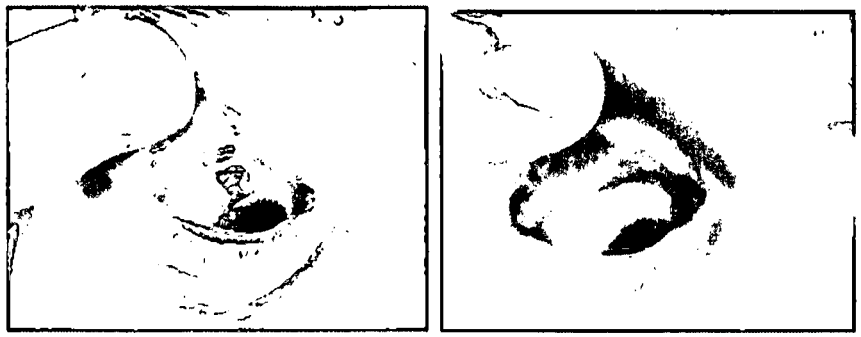
FIG. 7C is a graph showing the baseline-adjusted plasminogen activity of Subject 2 at 5-15 minutes, 1 hour, 6 hours, 24 hours and 48 hours after the end of the infusion of a single dose of 2 mg/kg.
Figure 7C:
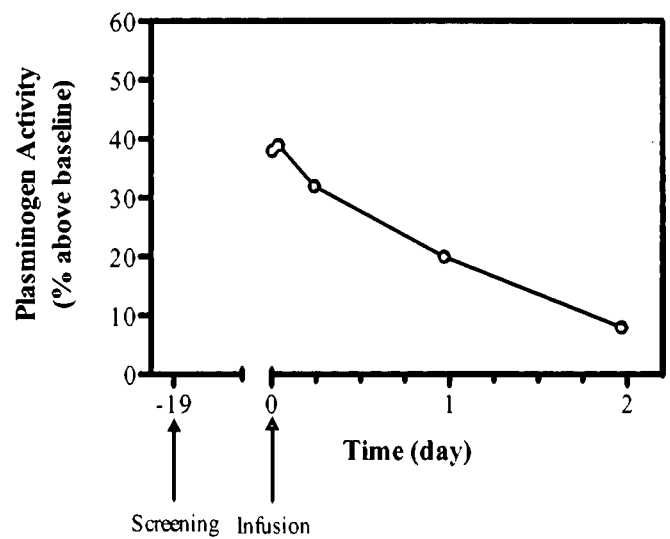

The baseline-adjusted plasminogen activity level of Subject 2 is reported at FIG. 7C from 5-15 minutes following the Plasminogen dose up to Day 2. It can be noted that the IV dose of 2 mg/kg has succeeded to raise the plasminogen activity above its initial level for at least 2 days. Based on FIG. 5, it can be concluded that the administration of a dose of about 2 mg/kg of mass of the plasminogen-deficient subject per day or every-two-day is sufficient to increase the subject plasminogen activity level by about 10% of the normal plasminogen activity, and therefore it would be also sufficient to increase it by 5% or 1% of the normal plasminogen activity.

Example 3: Repeated Dose Modelisation Based on Single Dose Results of Example 2

Figure 6:
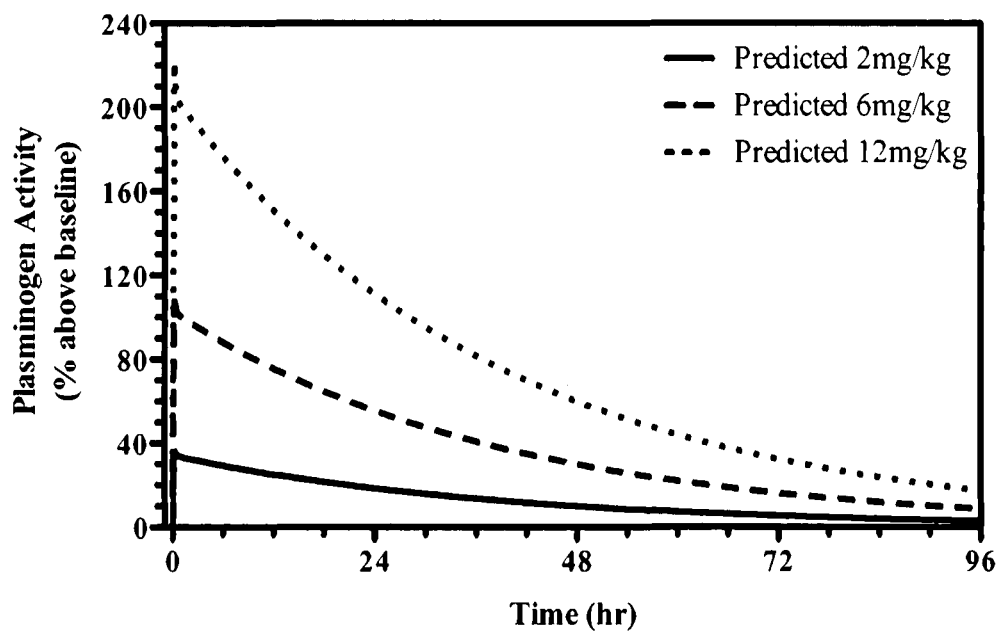
FIG. 6 is a graph showing the predicted PK (determined by said equation) for a single dose of 2 mg/kg, 6 mg/kg and 12 mg/kg.

Based on the equation determined with the application Phoenix® WinNonlin (see Example 2a), it is possible to predict the curve of elimination of the Glu-plasminogen (or the PK profile) in a plasminogen-deficient subject at any dose. The predicted curves for the administration of a single dose of 2, 6 and 12 mg/kg over a period of 96 hours are reported at FIG. 6.

Figure 8A:
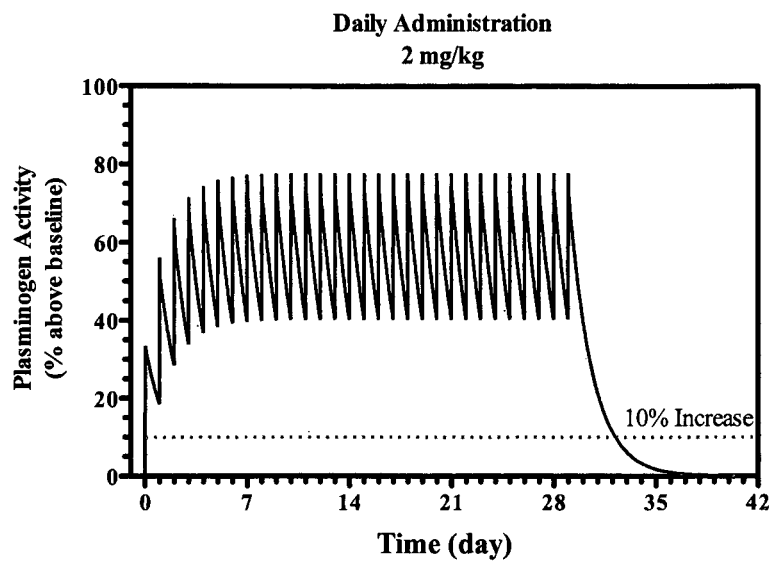
FIG. 8A is a graph showing the predicted pharmacokinetic profile of the plasmatic plasminogen activity (above baseline) for a daily administration of 2 mg/kg of Glu-plasminogen in a plasminogen-deficient subject.
Figure 8B:
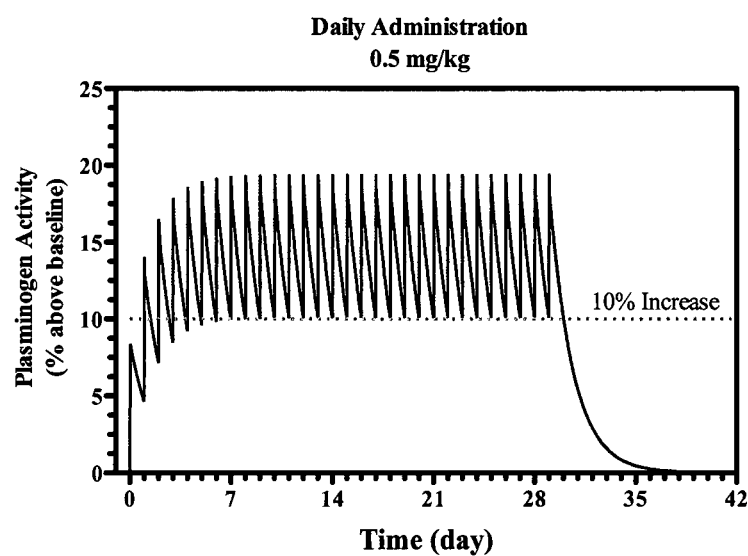
FIG. 8B is a graph showing the predicted pharmacokinetic profile of the plasmatic plasminogen activity (above baseline) for a daily administration of 0.5 mg/kg of Glu-plasminogen in a plasminogen-deficient subject.
Figure 9A:
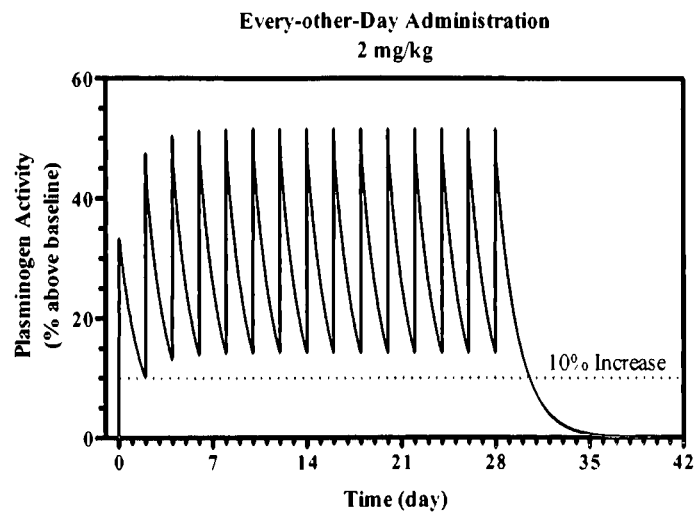
FIG. 9A is a graph showing the predicted pharmacokinetic profile of the plasmatic plasminogen activity (above baseline) for an every-other-day administration of 2 mg/kg of Glu-plasminogen in a plasminogen-deficient subject.
Figure 9B:
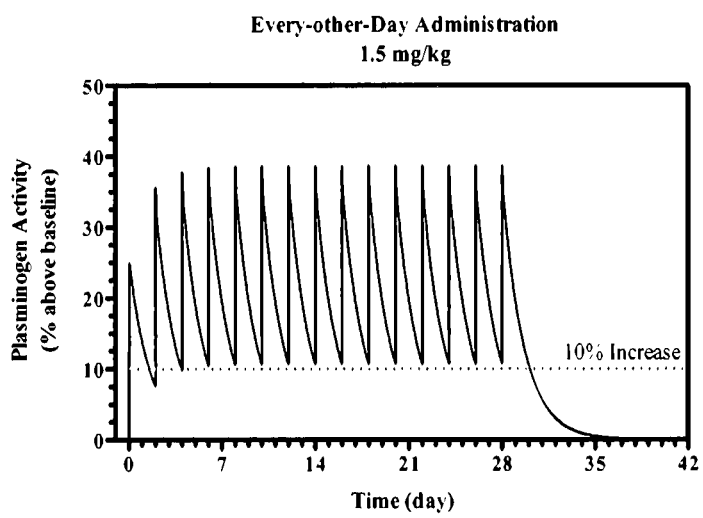
FIG. 9B is a graph showing the predicted pharmacokinetic profile of the plasmatic plasminogen activity (above baseline) for an every-other-day administration of 1.5 mg/kg of Glu-plasminogen in a plasminogen-deficient subject.
Figure 10A:
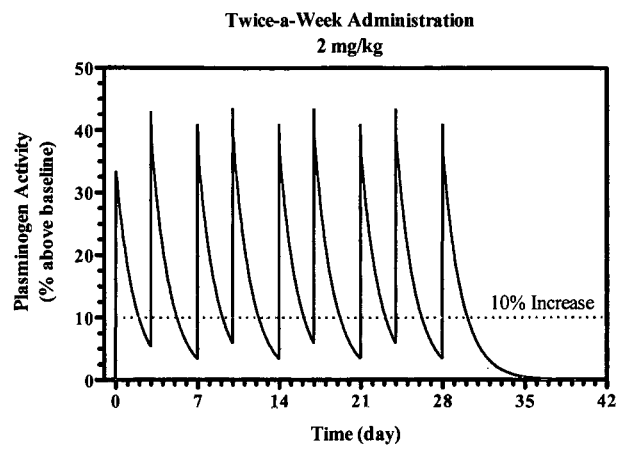
FIG. 10A is a graph showing the predicted pharmacokinetic profile of the plasmatic plasminogen activity (above baseline) for a twice-a-week administration of 2 mg/kg of, Glu-plasminogen in a plasminogen-deficient subject.
Figure 10B:
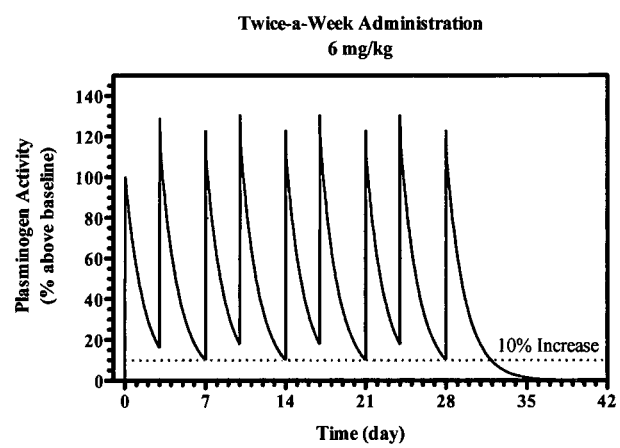
FIG. 10B is a graph showing the predicted pharmacokinetic profile of the plasmatic plasminogen activity (above baseline) for a twice-a-week administration of 6 mg/kg of Glu-plasminogen in a plasminogen-deficient subject.
Figure 10C:
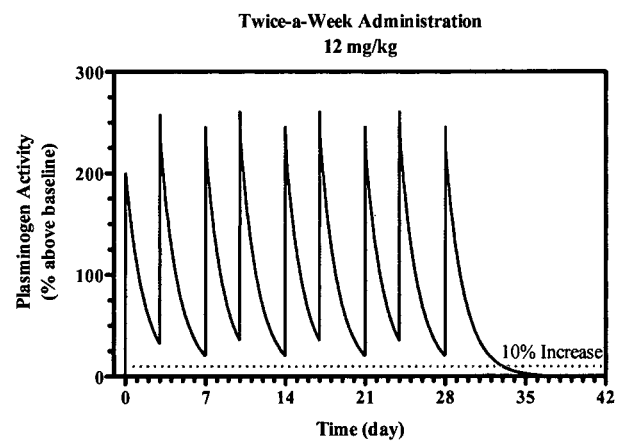
FIG. 10C is a graph showing the predicted pharmacokinetic profile of the plasmatic plasminogen activity (above baseline) for a twice-a-week administration of 12 mg/kg of Glu-plasminogen in a plasminogen-deficient subject.
Figure 11A:
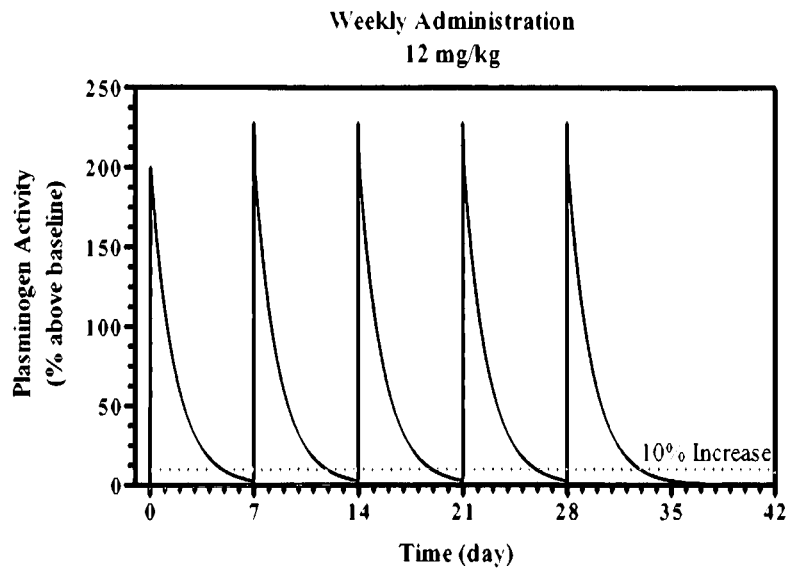
FIG. 11A is a graph showing the predicted pharmacokinetic profile of the plasmatic plasminogen activity (above baseline) for a weekly administration of 12 mg/kg of Glu-plasminogen in a plasminogen-deficient subject.
Figure 11B:
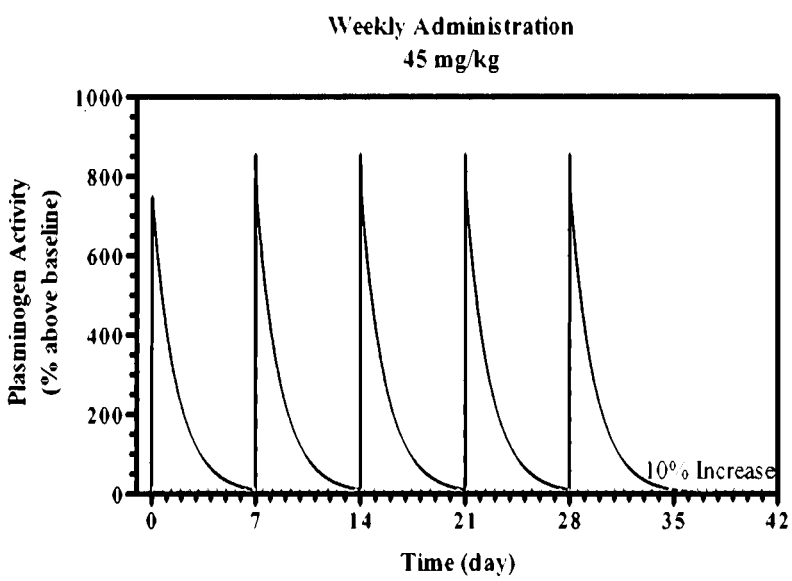
FIG. 11B is a graph showing the predicted pharmacokinetic profile of the plasmatic plasminogen activity (above baseline) for a weekly administration of 45 mg/kg of Glu-plasminogen in a plasminogen-deficient subject.

Based on this equation, predictions have been performed for repeated doses with different frequencies of administration: every day, every two days, twice a week and once a week. Various combinations of doses and frequencies have been evaluated using this equation. FIGS. 8A and 8B represent the baseline-adjusted plasminogen activity for a daily administration of doses of 2 mg/kg and 0.5 mg/kg, respectively. FIGS. 9A and 9B represent the baseline-adjusted plasminogen activity for an every-other-day administration of doses of 2 mg/kg and 1.5 mg/kg, respectively. FIGS. 10A, 10B and 10C represent the baseline-adjusted plasminogen activity for a twice-a-week administration of doses of 2 mg/kg, 6 mg/kg and 12 mg/kg. FIGS. 11A and 11B represent the baseline-adjusted plasminogen activity for a weekly administration of doses of 12 mg/kg and 45 mg/kg, respectively. The level of plasminogen activity corresponding to the level of troughs and peaks during the steady-state for each of these frequencies of administration and doses are reported in Table 2.

With these predictions, it has been possible to determine the minimal dose that is necessary to raise the level of plasminogen activity (trough level at steady-state) by at least 1% or by at least 10% of the normal plasminogen activity above baseline. The baseline represent the subject's own plasminogen activity before treatment. Table 2 is useful to determine the combinations of dose & frequency that result in an increase of at least 1% of the normal plasminogen activity and an increase of at least 10% of the normal plasminogen activity. It has been found that the minimal dose necessary to raise the trough plasminogen activity level by a minimum of at least 10% of the normal plasminogen activity is about 0.5 mg/kg in a daily administration, about 1.5 mg/kg in every-other-day administration, about 2.0 mg/kg in every-other-day administration, about 6 mg/kg in a twice-a-week administration, and about 45 mg/kg in a weekly administration. It has been found that the minimal dose necessary to raise the trough plasminogen activity level by a minimum of at least 1% of the normal plasminogen activity is about 2 mg/kg in a twice-a-week administration and about 12 mg/kg in a weekly administration. Obviously, other combinations of doses and frequencies can be evaluated by this equation, but the combinations reported in Table 2 give a good understanding of the realm of combinations that raise the trough plasminogen activity level by a minimum of at least 1%, 5% or 10%.

Table 2 also provides information about the maximal plasminogen activity level that can be reached in the subject's plasma (peak level at steady-state) resulting from each combination of dose & frequency. The goal of repeated administration is to find the best combinations of dose & frequency that allow the maintenance of plasminogen activity above the desired level (1%, 5% or 10% above the initial level), avoid to reach undesirable high peak values, and obtain a frequency of administration that is convenient for subject's compliance. In the present case, the undesirable high peak level has not been reached yet in clinical studies since no adverse effect has been observed in the combination of dose & frequency that have been tested.

Example 4: Repeated Doses of Glu-Plasminogen in a Pg-Deficient Human Baby

A male of Turkish descent was diagnosed at 4 weeks of age with congenital hypoplasminogenemia following presentation with typical ligneous conjunctivitis. The serum plasminogen activity level was inferior to 2%, and the diagnosis was confirmed by genetic testing showing a novel homozygous splice-site mutation in PLG (1587+1 G>A).

At 2 months of age, the subject suffered a severe respiratory syncytial virus (RSV) infection requiring ventilatory support for 5 days and a 1-month hospitalization. From this time, the subject had recurrent respiratory problems. From 4 months of age, the subject was treated with fresh frozen plasma (FFP) 20 mL/kg/week. At 18 months of age, the

TABLE 2

Figure 14:
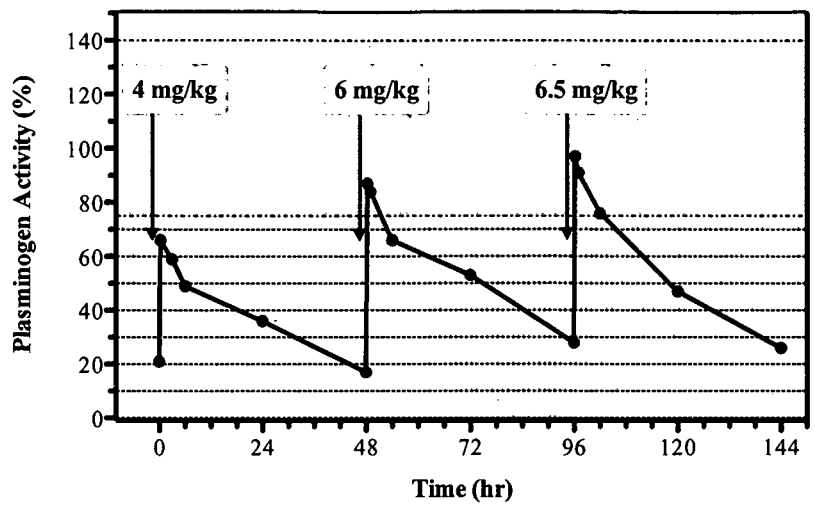
FIG. 14 shows the plasminogen activity and the timing of the plasminogen doses during the first 144 hours of the Glu-plasminogen supplementation in the subject of Example 4.

|  | Frequency | | | | | | | |
| --- | --- | --- | --- | --- | --- | --- | --- | --- |
|  | Daily | | Every-other-Day | | Twice-a-Week | | Weekly | |
| Dose | Peak | Trough | Peak | Trough | Peak | Trough | Peak | Trough |
| 0.5 mg/kg | 19 | 10 | — | — | — | — | — | — |
| 1.5 mg/kg | — | — | 39 | 10 | — | — | — | — |
| 2 mg/kg | 78 | 40 | 52 | 14 | 41 | 3 | — | — |
| 6 mg/kg | — | — | — | — | 123 | 10 | 115 | 1.4 |
| 12 mg/kg | — | — | — | — | 247 | 20 | 229 | 2.8 |
| 45 mg/kg | — | — | — | — | — | — | 859 | 10 | subject was found to have exophytic lesions within both the right and left main bronchi. The subject had one incident of acute severe dyspnea with cyanosis which responded to noninvasive oxygen insufflation. Subsequently, the subject had repeated bronchoscopies with laser removal of bronchial lesions with FFP cover. At 20 months of age, during preparation for bronchoscopy, the subject had an episode of acute cyanosis and cardiac arrest with asystole and was resuscitated after 30 minutes. Chest X-ray showed atelectasis of the left lung and of the right lower lobe (see FIG. 12). The subject was admitted to the ICU and required both ventilatory and circulatory support. Bronchoscopy has shown viscous secretions (see FIG. 13A) and obstructive lesions in the trachea (see FIG. 13B). Profuse viscous lung secretions were aspirated. Six days after the cardiac arrest event, the subject was given a first dose of Glu-plasminogen of 4 mg/kg, a second dose of 6 mg/kg, and subsequent doses of 6.5 mg/kg; each dose is given at every 48 hours. Plasminogen activity measurements, expressed in %, for the first 144 hours are shown in FIG. 14. It can be noted that the subject's baseline plasminogen activity before the first dose of Glu-plasminogen was 21%, which is most probably due to the previous FFP therapy. Following the Glu-plasminogen supplementation, progressive dissolution of the membranes and exophytic lesions with some blood spotting was noted, and was associated with a decrease in oxygen requirements. Improvement in the ligneous eye lesions was also observed. After 4 days of Glu-plasminogen treatment, the subject was extubated, but required reintubation 36 hours later due to exhaustion. One week after receiving the first dose of Glu-plasminogen, the subject was extubated again and the subject could then breathe normally. Plasminogen replacement has continued with a regimen of 6.5 mg/kg every second day. There was a progressive dissolution of the membranes with greatly reduced lesions seen after 6 weeks of Glu-plasminogen treatment. Supplementation of Glu-plasminogen in this severely affected patient has been very effective. All symptoms caused by its plasminogen-deficiency condition were either dissipated or significantly reduced. No significant side effect was observed. The efficacy of the Glu-plasminogen supplementation in the subject has been demonstrated by the observed clinical benefits.

Figure 15:
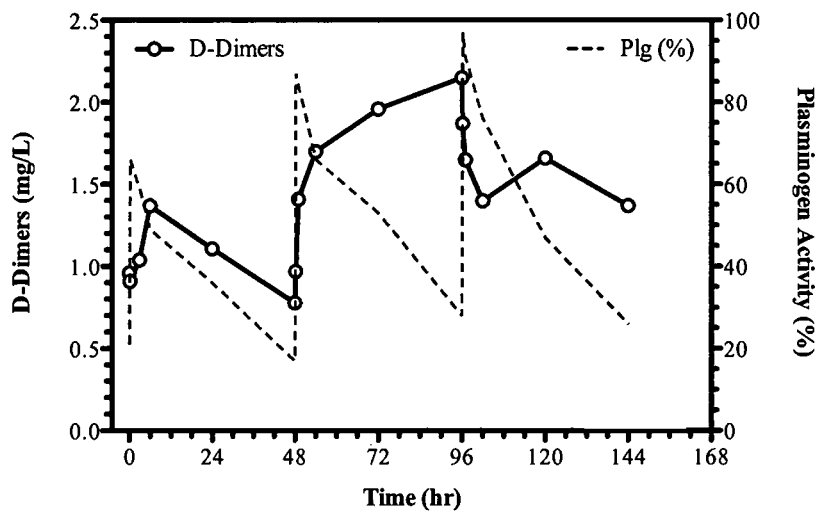
FIG. 15 shows the level of D-dimers and the plasminogen activity during the first 144 hours of Glu-plasminogen supplementation in the subject of Example 4.

In order to demonstrate that the supplemented Glu-plasminogen has efficiently degraded the fibrin, and was therefore actively treating the plasminogen-deficiency related conditions, the content in D-dimers has been measured. FIG. 15 superposes the profile of D-dimers and the profile of plasminogen activity level for the first 144 hours of the plasminogen supplementation in said subject. FIG. 15 shows that the peaks of D-dimers corroborate with the peaks of plasminogen activity. This confirms that the supplemented Glu-plasminogen was active in the subject.

Example 5: Single Dose (6 mg/kg) of Glu-Plasminogen in Pg-Deficient Human Subjects & PK Phase I study described in Example 2a has been pursued with the IV administration of a single dose of 6 mg/kg of Glu-plasminogen in cohort no. 2 containing seven human subjects, ranging from 14 to 38 years old. Their plasminogen activity baseline is reported in Table 3.

TABLE 3

| Cohort | Subject ID | Plasminogen activity (%) |
|---|---|---|
| 2 | 01-001-2 | 30 |
| | 01-002-2 | 52 |
| | 01-003-2 (pediatric) | 32 |
| | 01-005-2 (pediatric) | 37 |
| | 01-006-2 | 33 |
| | 01-007-2 | 19 |
| | 01-008-2 | 4 |

Figure 16:
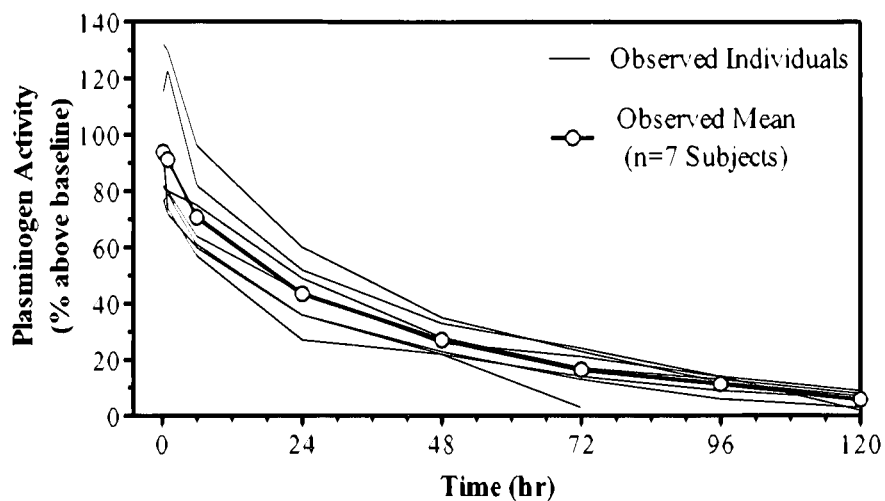
FIG. 16 is a graph showing the pharmacokinetic profile (PK) of the plasmatic plasminogen activity in seven plasminogen-deficient subjects that have received a single dose of 6 mg/kg of Glu-plasminogen, the mean values thereof and the curve for said mean values.
Figure 17:
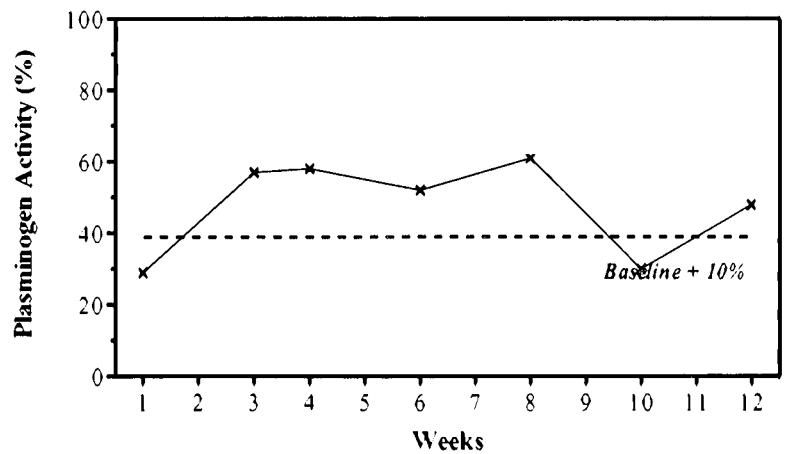
FIGS. 17 to 23 are graphs showing the plasminogen activity trough levels (plasmatic plasminogen activity detected prior a Glu-Plasminogen dose) measured during a 12-week period of Glu-plasminogen supplementation consisting of repeated doses of 6 mg/kg provided intravenously at every 2 days (qod) or at every 3 days (q3d). Trough levels of Subjects 01-001, 01-002, 01-006, 01-007, 01-008, 01-009 and 01-010 are reported in graphs of FIGS. 17, 18, 19, 20, 21, 22 and 23, respectively. Baseline+10% is illustrated for reference.
Figure 18:
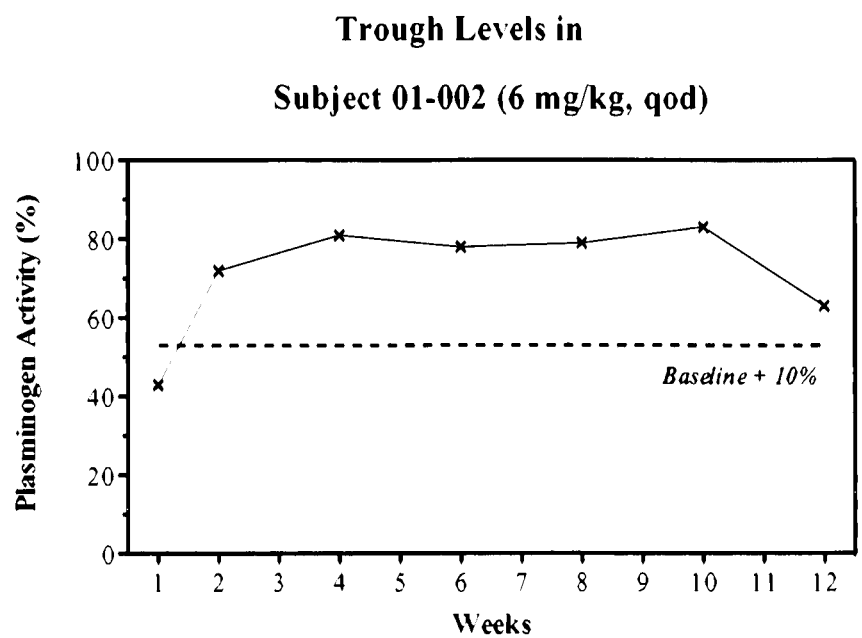
Figure 19:
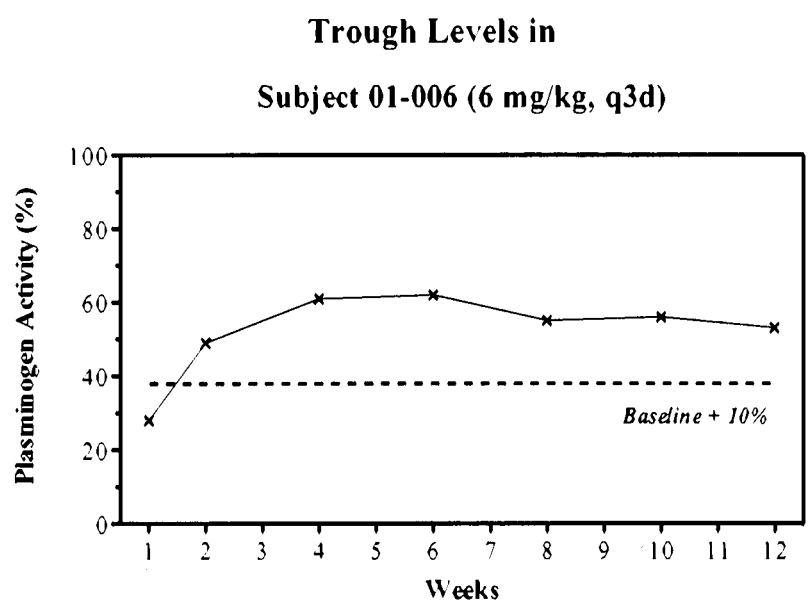
Figure 20:
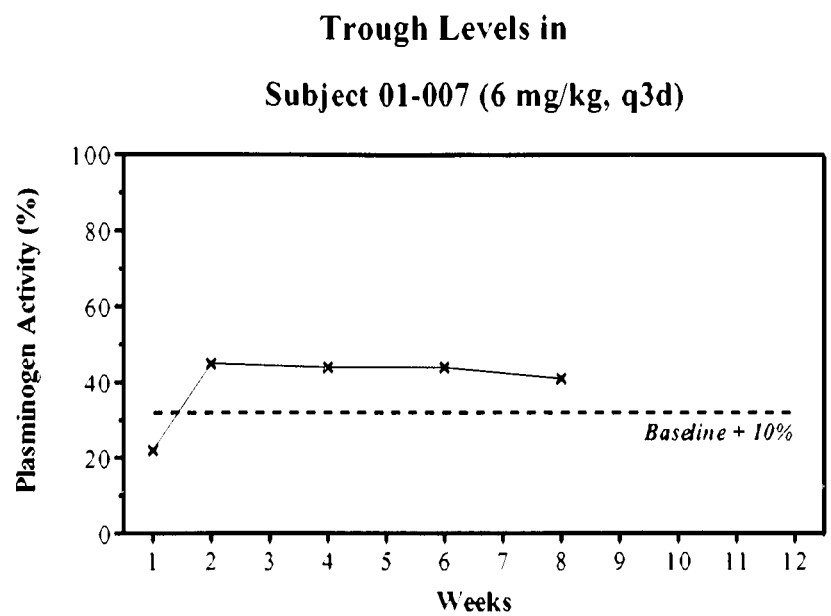
Figure 21:
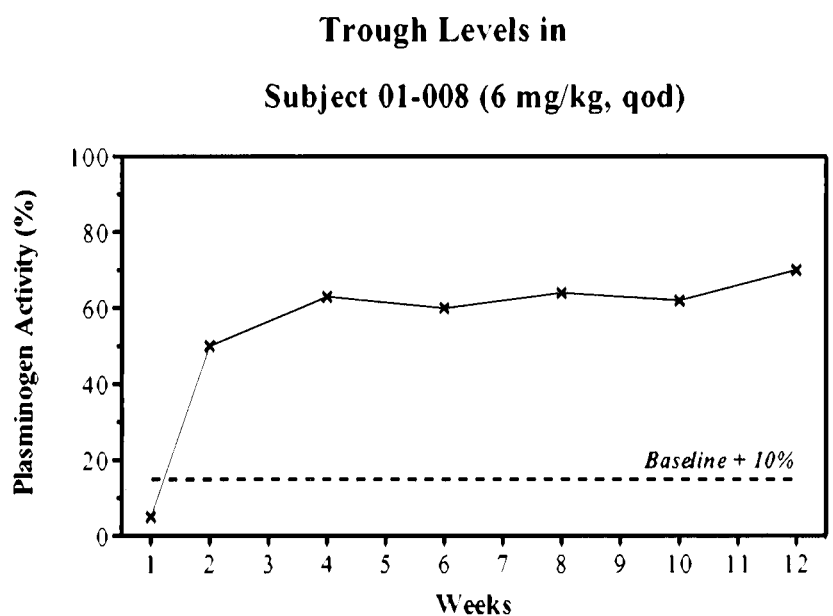
Figure 22:
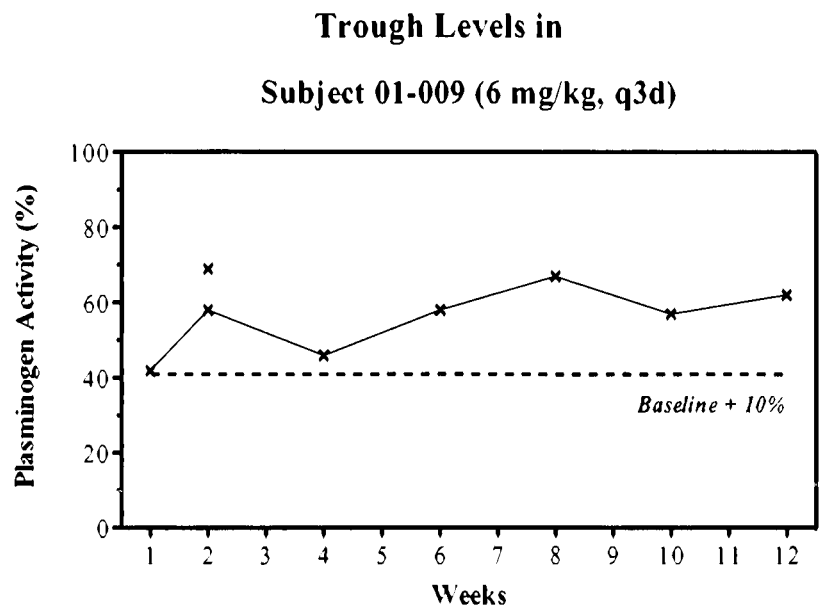
Figure 23:
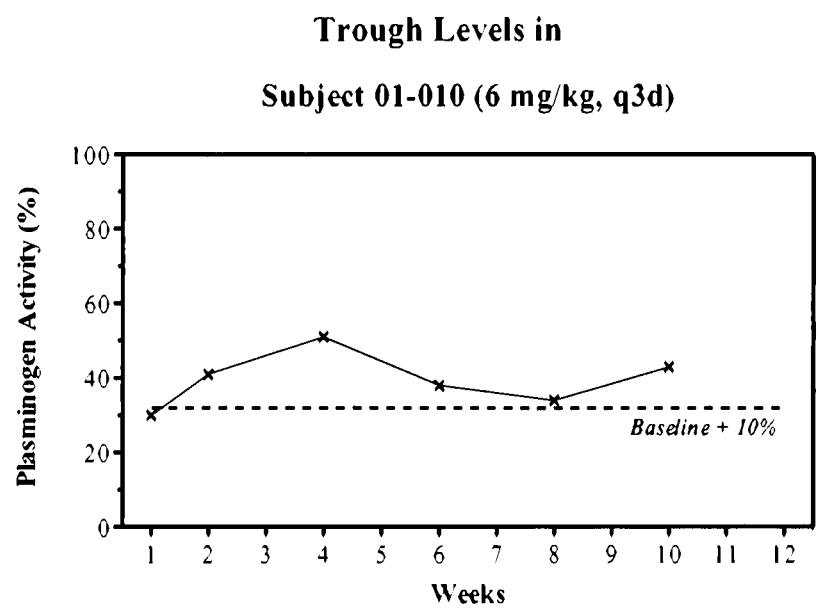

The baseline-adjusted plasminogen activity levels for each subject (thin line) during 120 hours are shown in FIG. 16 together with the mean value (opened circle) for each time point and the resulting mean curve (thick line). The observed mean values confirm that the administration of 6 mg/kg of Glu-plasminogen has resulted in a mean plasminogen activity level that is increased (relative to the baseline) by at least 10% of the normal plasminogen activity for a duration of 96 hours. The curve resulting from the mean values follows the pattern of the mathematical equation established by the mathematical equation determined with the application Phoenix® WinNonlin (Example 2a) and confirm that said equation adequately represents the PK profile of Glu-plasminogen in plasminogen-deficient human.

Individual terminal half-life has been determined and it ranges from 14.5 hours to 53.3 hours in Cohort 1 (2 mg/kg) and from 17.2 hours to 50.0 hours in Cohort 2 (6 mg/kg). Although large inter-subject variability was observed, there was no indication of non-linear kinetics. Data not shown for all subjects. The mean terminal half-life has been found relatively constant from the 2 mg/kg dose (35.6±17.6 hours) to the 6 mg/kg dose (35.7±12.3 hours).

Example 6: Repeated Doses (6 mg/kg) of Glu-Plasminogen in Pg-Deficient Human Subjects & PK In a pivotal Phase 2/3 study, doses of 6 mg/kg of Glu-Plasminogen were repeatedly administered in a cohort of nine plasminogen-deficient human subjects at the frequency of either i) every two days or every other day (qod), or ii) every three days (q3d). Their plasminogen activity baseline is reported in Table 4.

TABLE 4

| Patient | Frequency | Baseline Value (%) |
|---|---|---|
| 01-001 | q3d | 29 |
| 01-002 | qod | 43 |
| 01-006 | q3d | 28 |
| 01-007 | q3d | 22 |
| 01-008 | qod | <5 |
| 01-009 | q3d | 42 |
| 01-010 | q3d | 28 |
| 01-011 | q3d | 34 |
| 01-012 | q3d | 38 |

Every week or two, the plasminogen activity was monitored prior to the administration of the subsequent dose and said plasminogen activity prior to the dose infusion represents the trough level of the plasmatic plasminogen activity profile in the subject. The trough levels of Subjects 01-001, 01-002, 01-006, 01-007, 01-008, 01-009 and 01-010 are reported in separated graphs shown in FIGS. 17, 18, 19, 20, 21, 22 and 23, respectively. The dotted line represents the baseline value of the respective subject plus 10% of the normal plasminogen activity. This has been illustrated in each graph in order to easily compare the resulting increase with an increase of 10% of the normal plasminogen activity.

In all subjects, the trough level was raised at least 10% of the normal plasminogen activity after the first week (identified as Week 2) of Glu-plasminogen supplementation. Subject 01-001 has started to be monitored at Week 3, not at Week 2.

In all subjects (except for subject 01-001), the trough level was maintained above 10% of the normal plasminogen activity for the whole duration of the monitored Glu-plasminogen supplementation. In subject 01-001, the trough level went down to 30% at week 10, which represent 1% above its own baseline value and went back up at the next monitored week (Week 12). There has been a discontinuation in the treatment of this subject between Week 8 and Week 10, and this is most probably the reason why its plasminogen activity level went down and went back up after the supplementation has been resumed. Therefore, the Glu-plasminogen supplementation of 6 mg/kg every three days (q3d) has successfully raised and maintained the plasminogen activity by at least 1% of the normal plasminogen activity over the supplementation period, and more particularly, by at least 10% of the normal plasminogen activity over the supplementation period.

Furthermore, the Glu-plasminogen supplementation of 6 mg/kg every two days (qod) has also successfully raised and maintained the plasminogen activity by at least 1% of the normal plasminogen activity over the supplementation period, and more particularly, by at least 10% of the normal plasminogen activity over the supplementation period.

As described herein, the accumulation period lasts generally up to 3 to 5 times the half-life of a compound in a subject's plasma. In the plasminogen-deficient subjects of the Phase I study, the half-life of Glu-plasminogen has been determined to be about 35.7 hours or 1.5 day (see Example 5). Thus, based on the determined half-life, the accumulation period would take from 107 hours (4.5 days) to 179 hours (7.4 days). It can be observed in FIGS. 17, 18, 19, 20, 21, 22 and 23 that the steady-state starts after about one week from the beginning of the supplementation period. This corroborates with the half-life of Glu-plasminogen in a plasminogen-deficient subject, which has been determined herein. Again, there is variability of the consumption of the plasminogen is an individual subject from time to time due to many factors that results in an observed trough level curve that differs slightly from the theory as described in FIG. 4. Mean value brings the observation closely to the theory (not shown).

Example 7: Repeated Doses (6 mg/kg) of Glu-Plasminogen in Pg-Deficient Human Subjects & Efficacy One goal of the Glu-plasminogen supplementation of the present invention is to provide a Glu-plasminogen supplementation that is efficient to reduce and/or treat at least one plasminogen-deficiency related symptom. Phase II subjects were monitored for their visible lesions (Table 5), global improvement (Table 6) and quality of life (Table 6) at Day 0, Week 4, Week 8 and/or Week 12.

TABLE 5

| Subject | Visit | Visible Lesions | Total Number of Lesions | Location of Lesions | Measurable |
|---|---|---|---|---|---|
| 01-001 | Day 0 | Yes | 2 | Left eye | 10 × 2 mm |
|  |  | Yes | 2 | Right eye | 10 × 2 mm |
|  | Week 4 | No | 0 | — | — |
| 01-002 | Day 0 | Yes | 1 | Left eye | 15 × 5 mm |
|  | Week 4 | No | 0 | — | — |
| 01-006 | Day 0 | Yes | 1 | Upper gingiva | No |
|  | Week 4 | No | 0 | — | — |
|  | Week 8 | No | 0 | — | — |
| 01-007 | Day 0 | No | — | — | — |
|  | Week 4 | No | — | — | — |
| 01-008 | Day 0 | Yes | 7 | Left eye | No |
|  |  | Yes | 7 | Lower gingiva | No |
|  |  | Yes | 7 | Right eye | No |
|  |  | Yes | 7 | Upper gingiva | No |
|  | Week 4 | No | 0 | — | — |
|  | Week 8 | No | 0 | — | — |
|  | Week 12 | No | 0 | — | — |
| 01-009 | Day −4 | No | — | — | — |
|  | Week 4 | No | — | — | — |
| 01-010 | Day −4 | Yes | 2 | Right Eye, low lid | 10 × 5 mm |
|  |  | Yes | 2 | Right Eye, up lid | 15 × 5 mm |
|  | Week 4 | Yes | 2 | Right Eye, low lid | 1 × 1 mm |
|  |  | Yes | 2 | Right Eye, up lid | 5 × 2 mm |

It can be noted from the visible lesions monitoring that some lesions have been reduced such as in subject 01-010, or completely eliminated at Week 4 such as in subjects 01-001, 01-002, 01-006 and 01-008, or have not occurred in subjects 01-009, which had no visible lesions at Day 0. Therefore, the Glu-plasminogen supplementation of the present invention reduces lesion, treat lesion or prevent lesion in plasminogen-deficient subject.

TABLE 6

| Subject | Visit | CGI-I Score | Quality of Life Score |
|---|---|---|---|
| 01-001 | Day 0 | 0 - Not assessed | 10 - Go to work each day/normal daily activities |
|  | Week 4 | 1 - Very much improved | 10 - Go to work each day/normal daily activities |
| 01-002 | Day 0 | 0 - Not assessed | 10 - Go to work each day/normal daily activities |
|  | Week 4 | 1 - Very much improved | 10 - Go to work each day/normal daily activities |
| 01-006 | Day 0 | 0 - Not assessed | 7 - Work few hours daily/active at least 5 hours/day |
|  | Week 4 | 1 - Very much improved | 9 - Work 8 hours daily/take part in family life |
|  | Week 8 | 1 - Very much improved | 9 - Work 8 hours daily/take part in family life |
| 01-007 | Day 0 | 0 - Not assessed | 10 - Go to work each day/normal daily activities |
|  | Week 4 | 4 - No change | 10 - Go to work each day/normal daily activities |
| 01-008 | Day 0 | 4 - No change | 7 - Work few hours daily/active at least 5 hours/day |
|  | Week 4 | 1 - Very much improved | 9 - Work 8 hours daily/take part in family life |
|  | Week 8 | 1 - Very much improved | 10 - Go to work each day/normal daily activities |
|  | Week 12 | 1 - Very much improved | 10 - Go to work each day/normal daily activities |
| 01-009 | Day -4 | 0 - Not assessed | 10 - Go to work each day/normal daily activities |
|  | Week 4 | 2 - Much improved | 10 - Go to work each day/normal daily activities |
| 01-010 | Day -4 | 0 - Not assessed | 10 - Go to work each day/normal daily activities |
|  | Week 4 | 1 - Very much improved | 10 - Go to work each day/normal daily activities |

The global improvement was assessed by using the question and responses detailed in FIG. 24.

In Table 6, it can be noted that most subjects have experienced a great improvement of their clinical global impression at Week 4, which has remained improved for the whole duration of the monitored period. More particularly, the CGI score had either 'very much improved' or 'much improved', except for subject 01-007 for which it had not changed. Therefore, the plasminogen supplementation is successful to improve an impaired clinical global impression.

The quality of life was assessed by using the scale developed by the American Chronic Pain Association, which is commonly used for the evaluation of the quality of life in any patients. The quality of life scale detailed in FIG. 25.

In Table 6, it can be noted that the quality of life for those who were not already going to work each day or had normal daily activities (score 10), has improved at Week 4 and for one of them it has continued to improve at Week 8. For the subjects having a score of 10 at Day 0, they have maintained their good quality of life during the monitored period. Therefore, it can be concluded that the Glu-plasminogen supplementation improves the quality of life for the subject who has an impaired quality of life or a quality of life score lower than 10.

Headings are included herein for reference and to aid in locating certain sections These headings are not intended to limit the scope of the concepts described therein, and these concepts may have applicability in other sections throughout the entire specification. Thus, the present invention is not intended to be limited to the embodiments shown herein but is to be accorded the widest scope consistent with the principles and novel features disclosed herein. The singular forms "a", "an" and "the" include corresponding plural references unless the context clearly dictates otherwise. Unless otherwise indicated; all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

The invention claimed is:

1. A method for increasing plasminogen activity level in a plasminogen-deficient human subject having a Type I or Type II plasminogen-deficiency, wherein the plasminogen-deficient human subject has a reduced plasmatic plasminogen activity relative to a normal plasmatic plasminogen activity, the method comprising intravenously administering to the plasminogen-deficient human subject a repeated effective dose of Glu-plasminogen over a supplementation period, wherein the repeated effective dose comprises every-two-day, every-three-day, every-four-day or twice-a-week administration at a dose of 1.5 mg/kg to 12 mg/kg of weight of the plasminogen-deficient human subject, and wherein the method increases plasminogen activity level by at least about 10% of the normal plasminogen activity and to a level that is no more than about 300% of the normal plasminogen activity and maintains said increased plasminogen activity level over the supplementation period.

2. The method of claim 1, wherein the plasminogen-deficient human subject has a Type I plasminogen-deficiency.

3. The method of claim 1, wherein the plasminogen-deficient human subject has a Type II plasminogen-deficiency.

4. The method of claim 1, wherein the reduced plasmatic plasminogen activity is less than or equal to about 70% of the normal plasminogen activity.

5. The method of claim 1, wherein the plasminogen-deficient human subject suffers from ligneous conjunctivitis.

6. The method of claim 1, wherein the method increases plasminogen activity level by no more than about 150% of the normal plasminogen activity.

7. The method of claim 1, wherein the method increases plasminogen activity level by no more than about 100% of the normal plasminogen activity.

8. The method of claim 1, wherein the repeated effective dose comprises every-two-day administration at a dose of −1.5 mg/kg of weight of the plasminogen-deficient human subject.

9. The method of claim 1, wherein the repeated effective dose comprises twice-a-week administration at a dose of ~6 mg/kg of weight of the plasminogen-deficient human subject.

10. The method of claim 1, wherein the repeated effective dose comprises every-two-day, every-three-day, or every-four-day administration- at a dose of about 6 mg/kg of weight of the plasminogen-deficient human subject.

11. The method of claim 1, wherein the administered Glu-plasminogen is efficient to i) reduce, treat or prevent a plasminogen-deficiency related lesion, ii) improve an impaired clinical global impression, or iii) improve an impaired quality of life.

* * * * *

UNITED STATES PATENT AND TRADEMARK OFFICE
CERTIFICATE OF CORRECTION

PATENT NO. : 11,291,711 B2
APPLICATION NO. : 15/771454
DATED : April 5, 2022
INVENTOR(S) : Martin Robitaille et al.

Page 1 of 1

It is certified that error appears in the above-identified patent and that said Letters Patent is hereby corrected as shown below:

In the Claims

Column 30:
Line 51, Claim 3 "a Type H" should read -- a Type II --.
Line 66, Claim 8 "-1.5 mg/kg of weight" should read -- 1.5 mg/kg of weight --.

Column 31:
Lines 2-3, Claim 10 "-6 mg/kg of weight" should read -- 6 mg/kg of weight --.

Signed and Sealed this
Twenty-seventh Day of December, 2022

Katherine Kelly Vidal
*Director of the United States Patent and Trademark Office*